(12) United States Patent
Stewart et al.

(10) Patent No.: US 9,690,909 B2
(45) Date of Patent: Jun. 27, 2017

(54) METHODS AND APPARATUS FOR PROGRAMMING A MEDICAL PUMP

(71) Applicant: Baxter International Inc., Deerfield, IL (US)

(72) Inventors: Janice Stewart, Inverness, IL (US); Randolph Meinzer, Spring Grove, IL (US); Debra K. Bello, Vernon Hills, IL (US); Janet Mullan, Antioch, IL (US); James D. Jacobson, Lindenhurst, IL (US); Tuan Bui, Green Oaks, IL (US); Qui Chau, Skokie, IL (US)

(73) Assignee: Baxter International Inc., Deerfield, IL (US)

( * ) Notice: Subject to any disclaimer, the term of this patent is extended or adjusted under 35 U.S.C. 154(b) by 183 days.

(21) Appl. No.: 13/951,155

(22) Filed: Jul. 25, 2013

(65) Prior Publication Data

US 2014/0058350 A1   Feb. 27, 2014

Related U.S. Application Data

(63) Continuation of application No. 10/855,873, filed on May 27, 2004, now Pat. No. 8,518,021.

(51) Int. Cl.
G06F 19/00 (2011.01)
A61M 5/172 (2006.01)
(Continued)

(52) U.S. Cl.
CPC ......... *G06F 19/3468* (2013.01); *A61M 5/142* (2013.01); *A61M 5/14228* (2013.01);
(Continued)

(58) Field of Classification Search
CPC .. A61M 5/142; A61M 5/16827; A61M 5/172; A61M 2005/14208; G06F 19/325;
(Continued)

(56) References Cited

U.S. PATENT DOCUMENTS 4,624,661 A    11/1986 Airmond
4,731,051 A *  3/1988 Fischell .................. 604/67
(Continued)

FOREIGN PATENT DOCUMENTS

JP   2003-310557   11/2003
WO   96/36389      11/1996
(Continued)

OTHER PUBLICATIONS

Japanese Office Action for corresponding Japanese Application No. 2011-119762, dated Aug. 2, 2013.
(Continued)

*Primary Examiner* — Andrew Gilbert
(74) *Attorney, Agent, or Firm* — K&L Gates LLP

(57) ABSTRACT

A controller for a programmable medical pump comprises a memory including a plurality of preloaded infusion therapies, each preloaded infusion therapy including a plurality of program parameters. The controller also includes a device receiving a selection of one of the preloaded infusion therapies, profile data corresponding to a specific patient, and values for the program parameters. The controller further includes a processor configured to determine which of the plurality of program parameters to associate with the selected preloaded infusion therapy, determine limits for the associated program parameters based upon the selected preloaded infusion therapy and the profile data, determine if the received values of program parameters exceed the determined limits, and responsive to determining that the values of the program parameters are within the determined limits, cause the selected preloaded infusion therapy to be administered via the medical pump using the received values for the program parameters.

21 Claims, 16 Drawing Sheets

(51) Int. Cl.
*A61M 5/142* (2006.01)
*A61M 5/168* (2006.01)

(52) U.S. Cl.
CPC ......... *A61M 5/172* (2013.01); *A61M 5/16827* (2013.01); *A61M 2005/14208* (2013.01); *A61M 2205/3561* (2013.01); *A61M 2205/3569* (2013.01); *A61M 2205/3592* (2013.01); *A61M 2205/502* (2013.01)

(58) Field of Classification Search
CPC ............... G06F 19/326; G06F 19/3456; G06F 19/3462; G06F 19/3468; G06F 19/3475; G06F 19/3481
See application file for complete search history.

(56) References Cited

U.S. PATENT DOCUMENTS

| | | | |
|---|---|---|---|
| 5,088,981 A * | 2/1992 | Howson et al. | 604/31 |
| 5,681,285 A * | 10/1997 | Ford et al. | 604/151 |
| 5,685,844 A * | 11/1997 | Marttila | 604/65 |
| 5,713,856 A * | 2/1998 | Eggers et al. | 604/65 |
| 5,772,635 A | 6/1998 | Dastur et al. | |
| 5,781,442 A * | 7/1998 | Engleson et al. | 700/214 |
| 5,795,327 A | 8/1998 | Wilson et al. | |
| 6,012,034 A * | 1/2000 | Hamparian et al. | 705/2 |
| 6,070,761 A | 6/2000 | Bloom et al. | |
| 6,269,340 B1 | 7/2001 | Ford et al. | |
| 6,385,483 B1 | 5/2002 | Uber, III et al. | |
| 7,038,593 B2 | 5/2006 | Pederson | |
| 7,072,840 B1 * | 7/2006 | Mayaud | 705/2 |
| 7,384,410 B2 | 6/2008 | Eggers et al. | |
| 7,668,731 B2 * | 2/2010 | Martucci et al. | 705/2 |
| 7,835,927 B2 * | 11/2010 | Schlotterbeck et al. | 705/3 |
| 7,933,780 B2 * | 4/2011 | De La Huerga | 705/2 |
| 8,768,717 B2 * | 7/2014 | Blomquist | 705/2 |
| 2002/0169636 A1 * | 11/2002 | Eggers et al. | 705/3 |
| 2003/0163223 A1 * | 8/2003 | Blomquist | 700/282 |
| 2003/0204415 A1 * | 10/2003 | Knowlton | 705/2 |
| 2005/0177395 A1 * | 8/2005 | Blomquist | 705/2 |
| 2014/0095499 A1 * | 4/2014 | Blomquist | 707/736 |

FOREIGN PATENT DOCUMENTS

| | | |
|---|---|---|
| WO | 99/10029 | 3/1999 |
| WO | 02/069099 | 9/2002 |
| WO | 03/080157 | 10/2003 |
| WO | 03/094075 | 11/2003 |
| WO | 2004/012043 | 2/2004 |

OTHER PUBLICATIONS

Australian Office Action issued Feb. 8, 2012 for related Australian Appln. No. 201100005.
Canadian Office Action issued Dec. 13, 2012 for related Canadian Appln. No. 2,561,370.
Japanese Office Action issued Oct. 29, 2012 for related Japanese Appln. No. 2011-119762.
Israeli Office Action issued Jan. 29, 2013 for Israeli Appln. No. 177408.

* cited by examiner

METHODS AND APPARATUS FOR PROGRAMMING A MEDICAL PUMP

PRIORITY CLAIM

This application claims priority to and the benefit as a continuation application of U.S. patent application Ser. No. 10/855,873, filed May 27, 2004, now U.S. Pat. No. 8,518,021, entitled, "Apparatus and Method for Therapeutic Delivery of medication", the entire contents of which are hereby incorporated by reference and relied upon.

CROSS REFERENCE TO APPLICATIONS

This application expressly incorporates by reference, and makes a part hereof, the following U.S. patent and U.S. patent applications: U.S. Pat. No. 5,842,841; U.S. patent application Ser. No. 10/855,872; U.S. Pat. No. 7,927,313; and U.S. patent application Ser. No. 10/855,857, now U.S. Pat. No. 8,961,461.

TECHNICAL FIELD

This invention relates generally to an apparatus and method for programming medical devices, and, more particularly to an apparatus and method for programming medical or infusion therapies for a medical pump, such as an infusion pump.

BACKGROUND

Medications, both drugs and non-drugs, may be introduced into a patient with the use of an infusion device, or with a variety of other types of medical devices. However, a patient's response to an introduced medication is not always immediate. To encourage a faster patient response, clinicians may introduce drugs into a patient at a rate or dosage that is relatively high. One form of a relatively large rate or dosage of medication is known as a bolus dose. The purpose of the bolus dose is to hasten or magnify a patient response.

Additionally, certain types of drug deliveries into a patient are made to maintain the presence of a drug in a patient over a period of time. These deliveries are known as maintenance deliveries, or maintenance doses. Prior to a maintenance dose, it is sometimes necessary to quickly bring the quantity of the drug in the patient to a level at which it can be maintained. To establish this maintenance level, clinicians may deliver drugs into a patient at a relatively high rate or dosage. This initial relatively large rate or dosage of medication is known as a loading dose. The purpose of the loading dose is to establish a level of medication in a patient, after which a maintenance dose can be used to maintain that level. A bolus dose or loading dose may be delivered with fluid of a drug, non-drug, or test substance, and may be given by intravenous, epidural, subcutaneous, or arterial routes.

Modern infusion devices provide for the manual entry of data into the infusion device, enabling the device to control the infusion of medication into the patient. The data provided to such devices describes the infusion therapy, and includes parameters such as drug volume, infusion rate, and the total time for which the infusion is to be made. Some of these devices provide for the entry of data reflecting multiple regimens, thus enabling the device to automatically control multiple infusions concurrently or sequentially.

A limited number of infusion devices are equipped with a memory which may store parameter data for standard continuous infusion protocols. Such devices enable a clinician to recall parameter data from a standard continuous infusion from the memory of the device. This feature provides two distinct advantages to the clinician. First, parameter data may be recalled quickly from the memory, without the need for re-entry of the parameter data. Thus, these memory-equipped infusion devices have the advantage of typically being faster to program than non-memory-equipped infusion devices. Second, since parameter data may be stored and retrieved, the need for re-entry of parameter data is less necessary, and thus the human error associated with data entry is minimized. Memory-equipped infusion devices enable the recall of safe infusion regimens, thus dispelling the need for human entry of potentially erroneous regimen data. Such devices are limited to the storage of standard infusion therapies.

These devices, however, do not provide the ability for the storage or recall of therapy data which provide for a bolus dose or loading dose infusion. Furthermore, since these devices do not store bolus dose or loading dose therapy data in the memory of the device, they do not provide for error-checking of clinician-entered bolus dose or loading dose therapies.

Accordingly, a need has arisen for a controller for an infusion device which provides for the storage of bolus dose and loading dose infusion therapy data in the memory of the infusion device. Such a device would provide for the recall of safe bolus dose and loading dose infusion therapy data, and therefore would provide for both faster and safer bolus dose or loading dose infusion control. Furthermore, the need has arisen for a controller for an infusion device which provides for error-checking of clinician-entered bolus dose or loading dose infusion therapy data. Such a device would provide for safer bolus dose or loading dose infusions by comparing clinician-entered data to recommended parameter limits stored in the device's memory.

Additionally, it is common to provide a medication to a patient in response to certain patient and disease conditions. Under these circumstances, a clinician is required to determine an appropriate infusion therapy based upon the condition of the patient. Sometimes, the amount of time required by the clinician to determine an appropriate infusion therapy can be substantial and may delay necessary treatment to the patient. Furthermore, there is a risk that the clinician will not determine the appropriate medication therapy for the particular patient condition. For this additional reason, a need has been identified for a medical device that will provide pre-programmed infusion therapies based on patient and condition data.

The present invention is provided to solve these and other problems.

SUMMARY

The present invention provides an apparatus, system and method for programming and operating medical devices. The system and method may be used to program and operate medical devices, including infusion pumps.

According to one aspect of the present invention, a medical device is provided for delivering at least one of a bolus dose medication therapy and/or a loading dose medication therapy to a patient. The medical device comprises a medication delivery device having a memory, an input device and a processor. The memory is preloaded with medication therapies for at least one of a bolus dose medication therapy and/or a loading dose medication therapy. The input device of the medication delivery device receives program parameters for a first medication therapy. After the program parameters are received, the processor compares the received program parameters to the preloaded medication therapies.

According to another aspect of the present invention, the program parameters for a bolus dose medication therapy may comprise at least any one of a medication type, a medication concentration, a medication amount, an individual bolus volume, a total bolus volume, a bolus rate, a timing between bolus deliveries, and a patient weight.

According to another aspect of the present invention, the program parameters for a loading dose medication therapy may comprise at least any one of a medication type, a medication concentration, a loading dose volume, a loading dose rate, a loading dose time, a maintenance rate, a maintenance volume, a maintenance time, a diluent volume, and a patient weight.

According to another aspect of the present invention, after the processor compares the received program parameters to the preloaded medication therapies, the processor may provide an alarm. In one embodiment, the medication delivery device may have an alarm module for triggering an alarm when at least one of the program parameters for the first medication therapy is outside a parameter limit of the preloaded medication therapies.

According to another aspect of the present invention, the alarm may be a soft alarm or a hard alarm. When the alarm is a soft alarm, the controller allows the delivery of medication to the patient based on the received program parameters. The operator, however, does have the option to modify any of the program parameters after receiving a soft alarm. Conversely, when the alarm is a hard alarm, at least one of the input program parameters typically must be modified prior to allowing delivery of the medication.

According to another aspect of the present invention, after the processor compares the received program parameters to the preloaded medication therapies, the processor may request authorization prior to permitting the delivery of medication.

According to another aspect of the present invention, after the processor compares the received program parameters to the preloaded medication therapies, the processor may develop at least a part of a first medication therapy based on the received program parameters.

According to another aspect of the present invention, the input device of the medication delivery device receives program parameters for a second medication therapy. The second medication therapy may be one of a bolus dose medication therapy, a loading dose medication therapy or a standard infusion therapy. Again, the processor is provided for comparing the received program parameters for the second medication therapy to the preloaded medication therapies. After the processor processes the program parameters for the second medication therapy, the processor may issue an alarm, as described above, or it may develop at least a part of a second medication therapy based on the received program parameters. Additionally, the processor may develop a delivery schedule for delivery of the first medication therapy and the second medication therapy.

According to another aspect of the present invention, a programmable infusion pump having a memory, an input device and a processor is provided for delivering at least one of a bolus dose medication therapy and a loading dose medication therapy to a patient. The memory of the infusion pump is preloaded with medication therapies for at least one of a bolus dose medication therapy and a loading dose medication therapy. The input device receives program parameters for a first medication therapy for one of the bolus dose medication therapy and the loading dose medication therapy, and the processor compares the received program parameters to the preloaded medication therapies.

According to another aspect of the present invention, the programmable infusion pump has a plurality of independently programmable pumping channels. Each of the pumping channels is independently programmable for delivering at least one of the bolus dose medication therapy, the loading dose medication therapy and a standard infusion therapy. In one embodiment, a three channel pump is provided as such: the first pumping channel of the infusion pump is programmable for delivering the first medication therapy for one of the bolus dose medication therapy, the loading dose medication regimen and a standard infusion therapy; the second pumping channel of the infusion pump is programmable for delivering a second medication therapy for one of the bolus dose medication therapy, the loading dose medication therapy and the standard infusion regimen; and, the third pumping channel of the infusion pump is programmable for delivering a third medication therapy for one of the bolus dose medication therapy, the loading dose medication therapy and the standard infusion therapy. According to this aspect of the present invention, the processor may develop a delivery schedule for each pumping channel being utilized.

According to another aspect of the present invention, a system is provided for providing a bolus infusion therapy. The system comprises a controller for an infusion pump. The controller has a memory, a processor, and an input device. The controller may be a digital assistant. The memory contains preloaded bolus infusion therapies for a plurality of medications; the input device receives program parameters for a first bolus infusion regimen; and, the processor compares the received program parameters to the preloaded bolus infusion therapies in the memory of the controller.

According to another aspect of the present invention, in one embodiment the controller is an internal component of the infusion pump, and in another embodiment the controller is a separate and distinct component from the infusion pump. Typically, in both embodiments the controller develops a first bolus infusion therapy and transmits the first bolus infusion therapy to the infusion pump.

According to another aspect of the present invention, a system is provided for providing a loading dose infusion therapy. The system comprises a controller for an infusion pump, the controller having a memory, a processor, and an input device. The controller may be a digital assistant. The memory contains preloaded loading dose infusion therapies for a plurality of medications; the input device receives program parameters for a first loading dose infusion regimen; and, the processor compares the received program parameters to the preloaded loading dose infusion therapies in the memory of the controller.

According to another aspect of the present invention, in a first embodiment the controller is an internal component of the infusion pump, and in a second embodiment the controller is a separate and distinct component from the infusion pump. Typically, in both embodiments the controller develops a first loading dose infusion therapy and transmits the first loading dose infusion therapy to the infusion pump.

According to another aspect of the present invention, a method of programming an infusion therapy in an infusion pump is provided. The method comprises the steps of: providing a controller having a memory, a processor and an input device, wherein the memory is preloaded with medication therapies for at least one of a bolus dose medication therapy and a loading dose medication regimen; providing for receiving a first set of program parameters for a first medication therapy that is one of the bolus dose medication therapy and the loading dose medication regimen; providing for comparing the received program parameters to the preloaded medication therapies at the processor; and, providing for triggering an alarm when at least one of the program parameters for the first medication therapy is outside a parameter limit of the preloaded medication therapy ranges. Additionally, the method provides for receiving an override to the alarm.

According to another aspect of the present invention, an apparatus for programming a medication therapy for at least one of a bolus dose medication therapy and a loading dose medication therapy is provided. The apparatus comprises a controller having a memory, an interface and a processor. The memory is preloaded with medication therapies for at least one of a bolus dose medication therapy and a loading dose medication therapy. The interface is provided for receiving a selection of a first medication therapy type comprising at least one of a bolus dose medication therapy and a loading dose medication therapy, and the processor provides input screens specific to program parameters for the medication therapy type chosen.

According to another aspect of the present invention, a method of programming a medication therapy in a controller for an infusion pump is provided. The method comprises the steps of providing a controller having a memory, a processor and an interface device, wherein the memory is adapted to be preloaded with medication therapies for at least one of a bolus dose medication therapy and a loading dose medication therapy; providing for receiving a first medication therapy type comprising at least one of a bolus dose medication therapy and a loading dose medication therapy; and, providing for displaying an input screen that allows for receiving program parameters relevant to the received medication therapy.

According to another aspect of the present invention, a method of preloading a medication therapy in an infusion pump is provided. The method comprises the steps of providing a controller having a memory, a processor, and an input device, wherein the memory is capable of retrievably storing one or more preloaded medication therapies for at least one of a bolus dose medication therapy and a loading dose medication regimen; providing for receiving a set of program parameters for a medication therapy that describes at least one of a bolus dose medication therapy and a loading dose medication regimen; and, providing for retrievably storing the program parameters in the memory.

According to another aspect of the present invention, a controller for a programmable infusion pump is provided. The controller has a memory, an input device and a processor. The memory is preloaded with at least one of a plurality of patient profiles and condition profiles. The memory may further be preloaded with a plurality of associated medication therapies for a plurality of the profiles. The input device receives profile data comprising at least one of a patient profile data and a condition profile data for a specific patient, and the processor processes the received profile data and provides as output a medication therapy based on the processed profile data. Typically, the processor selects the medication therapy from the preloaded medication therapies corresponding to the preloaded profiles.

According to another aspect of the present invention, the memory is also preloaded with a plurality of medication profiles, and with an associated medication therapy for a plurality of the medication profiles. Generally, the preloaded medication profiles comprise data for at least one of a drug, a non-drug and a diluent. Additionally, the medication therapy generally comprise at least one of a dose, a rate, a concentration and a medication type.

According to another aspect of the present invention, the preloaded patient profiles comprise data for at least one of a patient pain state, a chronologic age, an age group, and a gestational age. Further, the preloaded condition profiles comprise data for at least one of a medical condition and a medical disease state.

According to another aspect of the present invention, the medication therapy provided by the processor comprises a medication type and delivery parameters. The delivery parameters generally comprise at least one of a dose, a rate and a concentration.

According to another aspect of the present invention, a controller for a programmable infusion pump is provided. The controller has a medication delivery therapy of at least one of a bolus dose medication therapy and a loading dose medication therapy. The controller also has a memory, an input device and a processor. The memory is preloaded with at least one of a plurality of patient profiles and condition profiles, and for each profile the memory is further preloaded with at least one of a bolus medication therapy and a loading dose medication therapy. The input device receives profile data comprising at least one of a patient data and a condition data for a specific patient. The processor processes the received profile data and provides as output at least one of the preloaded bolus medication therapies and preloaded loading dose medication therapies based on the processed profile data.

According to another aspect of the present invention, the controller selects the medication therapy from the preloaded bolus medication therapies and loading dose medication therapies corresponding to the preloaded profiles.

According to another aspect of the present invention, a method of programming an infusion therapy in a controller having a memory, a processor and an input device is provided. The method comprises the steps of: providing for preloading the memory with at least one of a plurality of patient profiles and condition profiles, and with an associated medication therapy for a plurality of the profiles; providing for receiving profile data comprising at least one of a patient profile data and a condition profile data for a specific patient; and, providing for processing the received profile data and for providing as output one of the preloaded medication therapies based on the processed profile data.

According to yet another aspect of the present invention, a method of programming an infusion therapy in an infusion pump is provided. The method comprises the steps of: providing for receiving a set of patient profile parameters that describe at least one of medication type, patient condition, and disease state; providing a controller having a memory, a processor, and an input device, wherein the memory is capable of retrievably storing one or more medication therapies for at least one of a bolus dose medication therapy and a loading dose medication therapy, wherein at least one of the medication therapies matches at least one set of patient profile parameters; providing for comparing the patient profile parameters to the medication therapies stored in the memory at the processor; and, providing for transmitting a medication therapy that matches the patient profile parameters.

According to another aspect of the present invention, a method of programming an medication therapy in a controller for an infusion pump is provided. The method comprises the steps of providing a controller having a memory, a processor and an interface device, wherein the memory is adapted to be preloaded with medication therapies for at least one of a bolus dose medication therapy and a loading dose medication therapy; providing for receiving a first medication therapy type comprising at least one of a bolus dose medication therapy and a loading dose medication therapy; providing for receiving a first medication type; and, providing for displaying a suggested first medication therapy for the selected medication therapy type and medication type.

According to another aspect of the present invention, the method further comprises at least one of the steps of providing for receiving program parameters relevant to the received medication therapy type; providing for receiving changes to at least one program parameter of the suggested first medication therapy; providing for comparing the received program parameters to the preloaded medication therapies; and, providing for triggering an alarm when at least one of the program parameters for the first medication therapy is outside a parameter limit for the preloaded medication therapy.

According to yet another aspect of the present invention, a method of programming a patient profile into the memory, and matching the patient profile with a recommended bolus/loading dose therapy is provided. The method comprises the steps of: providing a controller having a memory, a processor, and an input device, wherein the memory is capable of retrievably storing one or more sets of patient profile parameters that describe at least one of medication type, patient condition, and disease state, and wherein the memory is capable of storing one or more medication therapies for at least one of a bolus dose medication therapy and a loading dose medication regimen; providing for receiving a set of patient profile parameters that describe at least one of medication type, patient condition, and disease state; providing for matching the received set of patient profile parameters to at least one of a bolus dose medication therapy and a loading dose medication regimen; providing for retrievably storing the received set of patient profile parameters in the memory; and, providing for retrievably storing data in the memory, wherein the data reflects a correspondence between at least one set of patient profile parameters and at least one of a bolus dose medication therapy and a loading dose medication therapy.

According to another aspect of the present invention, a medication delivery controller is provided for an infusion pump for delivering at least one of a bolus dose and a loading dose. The medication delivery controller comprises a processor for cooperative interaction with a memory and an interface device. The memory is preloaded with medication therapies for at least one of a bolus dose medication therapy and a loading dose medication therapy. The interface device receives program parameters for a first medication therapy that is one of said bolus dose medication therapy, said loading dose medication therapy and a standard infusion therapy. The processor compares the received program parameters to the preloaded medication therapies. The medication delivery controller is a controller for an infusion pump. The infusion pump has a plurality of pumping channels, and wherein each of the pumping channels is independently programmable for delivering at least one of the bolus dose medication therapy, the loading dose medication therapy and the standard infusion therapy. The program parameters are necessary for the correct administration of the first medication therapy for a medicament. The program parameters for a bolus dose medication therapy for the medicament comprise at least one of a medication type, a medication concentration, a medication amount, a individual bolus volume, a total bolus volume, a bolus rate, a timing between bolus deliveries, and a patient weight. The program parameters for a loading dose medication therapy for the medicament, comprise at least one of a medication type, a medication concentration, a loading dose volume, a loading dose rate, a loading dose time, a maintenance rate, a maintenance volume, a maintenance time, a diluent volume, and a patient weight. The controller comprises an alarm module for setting an alarm when at least one of the program parameters for the first medication therapy is outside a parameter limit of the preloaded medication therapies. The alarm is a soft alarm allowing delivery of the medication to the patient based on the received program parameters for the first medication therapy. At least one of the controller and the interface device comprises an interface module for receiving an override for the soft alarm. At least one of the controller and the interface device comprises an interface module for receiving a change to at least one of the program parameters. The alarm is a hard alarm requiring a change to at least one of the program parameters for the first medication therapy. At least one of the controller and the interface device comprises an interface module for receiving a change to at least one of the program parameters. The processor and memory are structured to develop at least a part of the first medication therapy based on the received program parameters. The processor and memory are structured to develop a delivery schedule for the first medication therapy. The interface device is further provided for receiving program parameters for a second medication therapy for a medicament, that is one of a bolus dose medication therapy, a loading dose medication therapy and a standard infusion therapy, and wherein the processor is provided for comparing the received program parameters for the second medication therapy to the preloaded medication therapies. The processor and memory are structured to develop a delivery schedule for delivery of the first medication therapy and the second medication therapy. The controller further comprises an alarm module for setting an alarm when at least one of the program parameters for the second medication therapy is outside a parameter limit of the preloaded medication therapies. The alarm is a soft alarm allowing delivery of the medication to the patient based on the received program parameters for the second medication therapy. At least one of the controller and the interface device comprises an interface module for receiving an override for the alarm. At least one of the controller and the interface device comprises an interface module for receiving a change to at least one of the program parameters with the interface device. The alarm is a hard alarm requiring a change to at least one of the program parameters for the second medication therapy. At least one of the controller and the interface device comprises an interface module for receiving a change to at least one of the program parameters. A first pumping channel of the infusion pump is programmable for delivering the first medication therapy for one of the bolus dose medication therapy, the loading dose medication therapy and the standard infusion therapy.

According to another aspect of the present invention, a second pumping channel of the infusion pump is programmable for delivering a second medication therapy for one of said bolus dose medication therapy, said loading dose medication therapy and said standard infusion therapy. A third pumping channel of the infusion pump is programmable for delivering a third medication therapy for one of the bolus dose medication therapy, the loading dose medication therapy and the standard infusion therapy. The processor is further provided for developing a delivery schedule for the first medication therapy. The processor is further provided for developing a delivery schedule for at least one of the first, second, and third medication therapies. The interface device comprises a receiver for receiving information from an information identifier on a line set. The information identifier contains information comprising at least one of a patient name, age, sex, weight, allergies, condition, medication name, medication type, medication concentration, medication amount, individual bolus volume, total bolus volume, bolus rate, dose, timing between bolus deliveries, maximum number of boluses, maximum number of boluses per unit time, loading dose volume, loading dose rate, loading dose time, maintenance rate, maintenance volume, maintenance time, maintenance dose, diluent volume, patient profile data and condition profile data.

According to another aspect of the present invention, a system is provided for bolus infusion therapy. The system comprises a controller for an infusion pump. The controller has a memory, a processor, and an input device. The memory contains preloaded bolus infusion therapies for a plurality of medications. The input device receives program parameters for a first bolus infusion therapy, and the processor compares the received program parameters to the preloaded bolus infusion therapies in the memory of the controller. The controller is an internal component of the infusion pump. The controller may also be a separate and distinct component from the infusion pump. The controller develops the first bolus infusion therapy and transmits the first bolus infusion therapy to the infusion pump. The infusion pump comprises the controller.

According to another aspect of the present invention, a system is provided for loading dose infusion therapy. The system comprises a controller for an infusion pump. The controller has a memory, a processor, and an input device. The memory contains preloaded loading dose infusion therapies for a plurality of medications. The input device receives program parameters for a first loading dose infusion therapy, and the processor compares the received program parameters to the preloaded loading dose infusion therapies in the memory of the controller.

According to another aspect of the present invention, a system is provided for programming a medication therapy for at least one of a bolus dose medication therapy and a loading dose medication therapy. The system comprises a controller, a memory, and an interface device. The memory is adapted to be preloaded with medication therapies for at least one of a bolus dose medication therapy and a loading dose medication therapy. The interface device is structured to receive a selection of a first medication therapy type comprising at least one of a bolus dose medication therapy and a loading dose medication therapy. The interface device is structured to receive a medication type, and the processor is structured to provide a suggested first medication therapy for the selected medication therapy type and medication type. The interface device is structured to provide screens specific to receive program parameters for the first medication therapy for the selected medication therapy type. After the initial receipt of program parameters, the interface device is structured to receive changes to the program parameters for the first medication therapy. The controller is an integral part of a medication delivery device, and wherein the medication delivery device further comprises the memory and the interface device.

According to another aspect of the present invention, a method is provided for programming a medication therapy for use by a controller for an infusion pump. The method comprises the steps of providing a memory adapted to be preloaded with medication therapies for at least one of a bolus dose medication therapy and a loading dose medication therapy, receiving a first medication therapy type comprising at least one of a bolus dose medication therapy and a loading dose medication therapy, receiving a first medication type, and suggesting a first medication therapy for a selected medication therapy type and medication type. The memory is preloaded with medication therapies for at least one of a bolus dose medication therapy and a loading dose medication regimen. The method further comprises the steps of receiving a first set of program parameters for the first medication therapy type that is one of the bolus dose medication therapy and the loading dose medication therapy, comparing the received program parameters to the preloaded medication therapies, and triggering an alarm when at least one of the program parameters for the first medication therapy is outside a parameter limit of the preloaded medication therapy ranges. The method further comprises the step of providing a controller for the infusion pump for delivering the first medication therapy from the preloaded medication therapies. The method further comprises the step of providing an input device for receiving an information identifier from an infusion line set for use in programming the infusion therapy.

According to another aspect of the present invention, a line set is provided for interfacing with an infusion control system for delivering at least one of a bolus dose and a loading dose. The infusion control system comprises a processor and a memory for cooperative interaction with said processor. The memory comprises medication therapies for at least one of a bolus dose medication therapy and a loading dose medication therapy. The line set comprises a length of tube and a micro-electromechanical system (MEMS) element connected to said tube. The infusion control system further comprises an input device for receiving program parameters for a first medication therapy that is one of said bolus dose medication therapy, said loading dose medication therapy and a standard infusion therapy, said processor for comparing said received program parameters to said medication therapies in memory. The processor and the memory are housed with a controller for controlling the operation of said MEMS element. The controller has a displaying for displaying information. The infusion control system further comprises a central computer and a MEMS interface device, wherein said processor and said memory are located within said central computer, and wherein said central computer is location remote from said MEMS element and said MEMS interface device. The MEMS interface device comprises means for controlling and interrogating the MEMS element. The line set is disposable and wherein said MEMS interface device is reusable. The infusion control system further comprises an input device having a display for displaying information on the operation of said MEMS element, and having a reader for receiving an identifier. The identifier can also include an identification of the MEMS element, such as a MEMS pump, for forwarding this information along to the system and for tracking the operation and interaction of the MEMS element in relation to the system.

According to another aspect of the present invention, a medical infusion system is provided for infusing at least one of a bolus dose and a loading dose. The system comprises a disposable tube, a disposable electromechanical pump element connected to said tube, a pump interface device operably connectable to the pump element, a processor, and a memory for cooperative interaction with the processor. The memory comprises medication therapies for at least one of a bolus dose medication therapy and a loading dose medication therapy. The system further comprises a disposable reservoir attached to the disposable tube. The disposable reservoir comprises a valve which is structured to be controlled remotely.

According to another aspect of the present invention, a method is provided for delivering a medicament. The method comprises the steps of providing a tube having a MEMS pump attached thereto, the MEMS pump structured to operably connect to a pump interface device, a processor, and a memory for cooperative interaction with said processor. The memory comprises medication therapies for at least one of a bolus dose medication therapy and a loading dose medication therapy. The pump is activated using said pump interface device to deliver said medicament according to at least one of said bolus dose medication therapy and said loading dose medication therapy.

Other apparatuses, systems, methods, features, and advantages of the present invention will be, or will become, apparent to one having ordinary skill in the art upon examination of the following drawings and detailed description. It is intended that all such additional apparatuses, systems, methods, features, and advantages included within this description are within the scope of the present invention, and are protected by the accompanying claims.

BRIEF DESCRIPTION OF THE FIGURES

The specification can be better understood with reference to the following drawings. The components in the drawings are not necessarily to scale, emphasis instead being placed upon clearly illustrating the principles of the present invention. In the drawings, like reference numerals designate corresponding parts throughout the several views.

DETAILED DESCRIPTION

Figure 1:
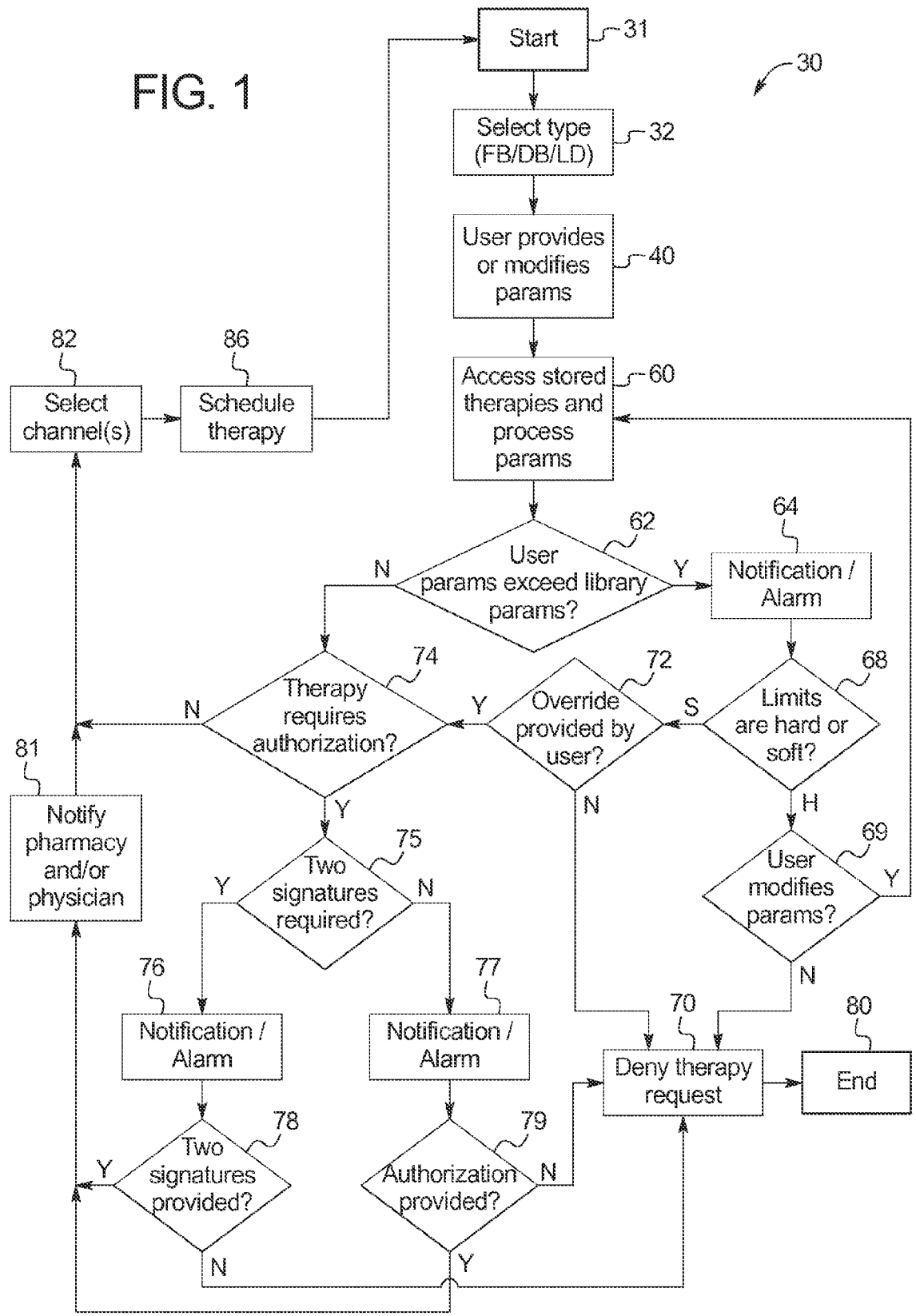
FIG. 1 is a flowchart depicting one embodiment of the medical device programming system of the present disclosure.
Figure 2:
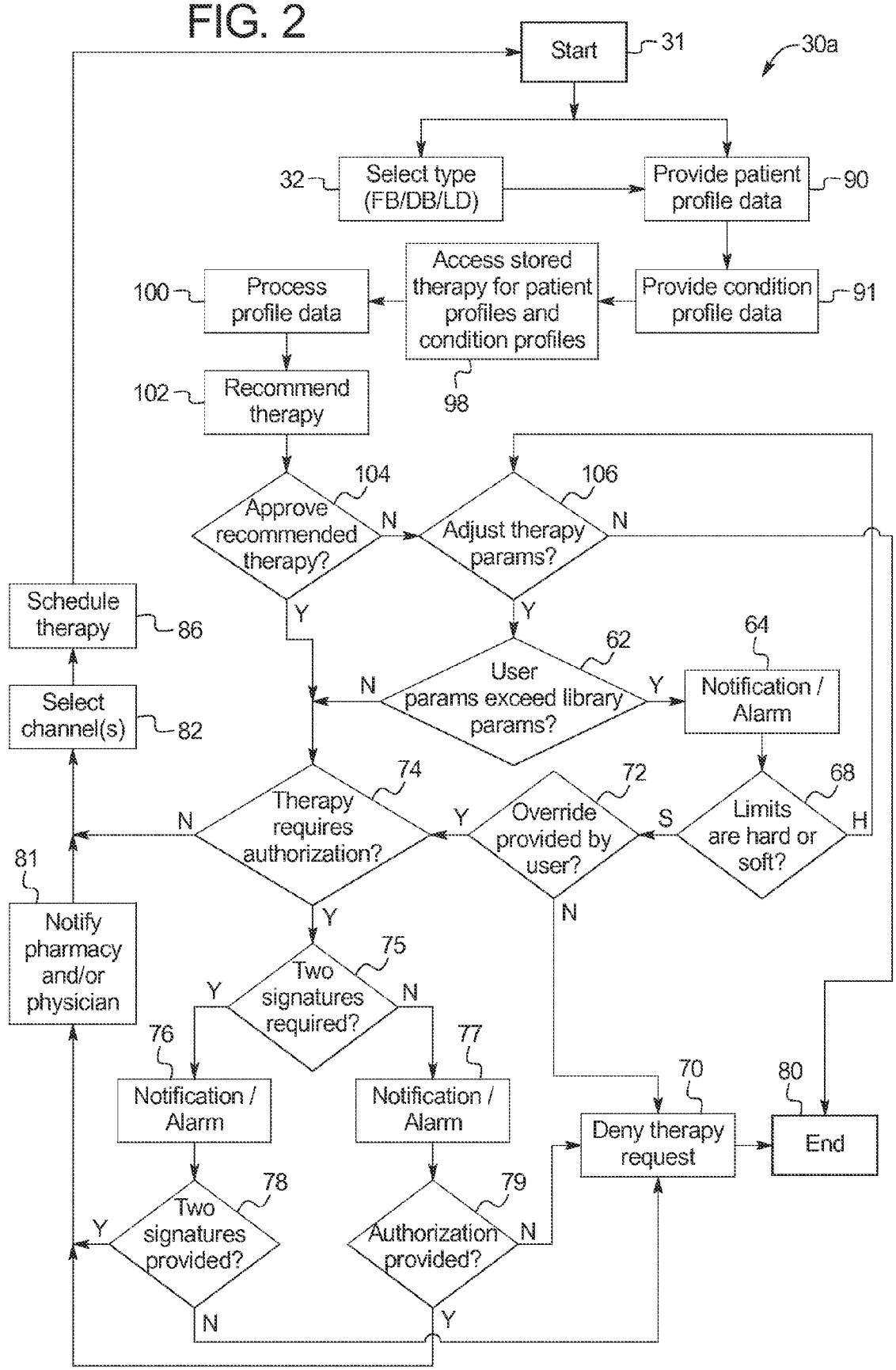
FIG. 2 is a flowchart depicting another embodiment of the medical device programming system of the present disclosure.

Referring to the Figures, and specifically to FIGS. 1 and 2, there are shown two flowcharts identifying systems and methods for programming a medical device to deliver a medication therapy to a patient. A person having ordinary skill in the art would fully understand that the present system is designed to operate for the programming of any type of medical device to deliver a medication to a patient. For illustrative purposes only, this detailed description focuses on an infusion pump as the medical device to deliver a drug and/or a non-drug to the patient. Further, it is understood that infusion pumps incorporate a variety of types of medical pumps, including but not limited to volumetric infusion pumps, peristaltic pumps, cassette pumps and syringe pumps, and can apply to delivery mode applications such a intravenous delivery, intramuscular delivery, IA delivery, epidural delivery, irrigation of fluid spaces, and other types of delivery and uses.

Figure 3:
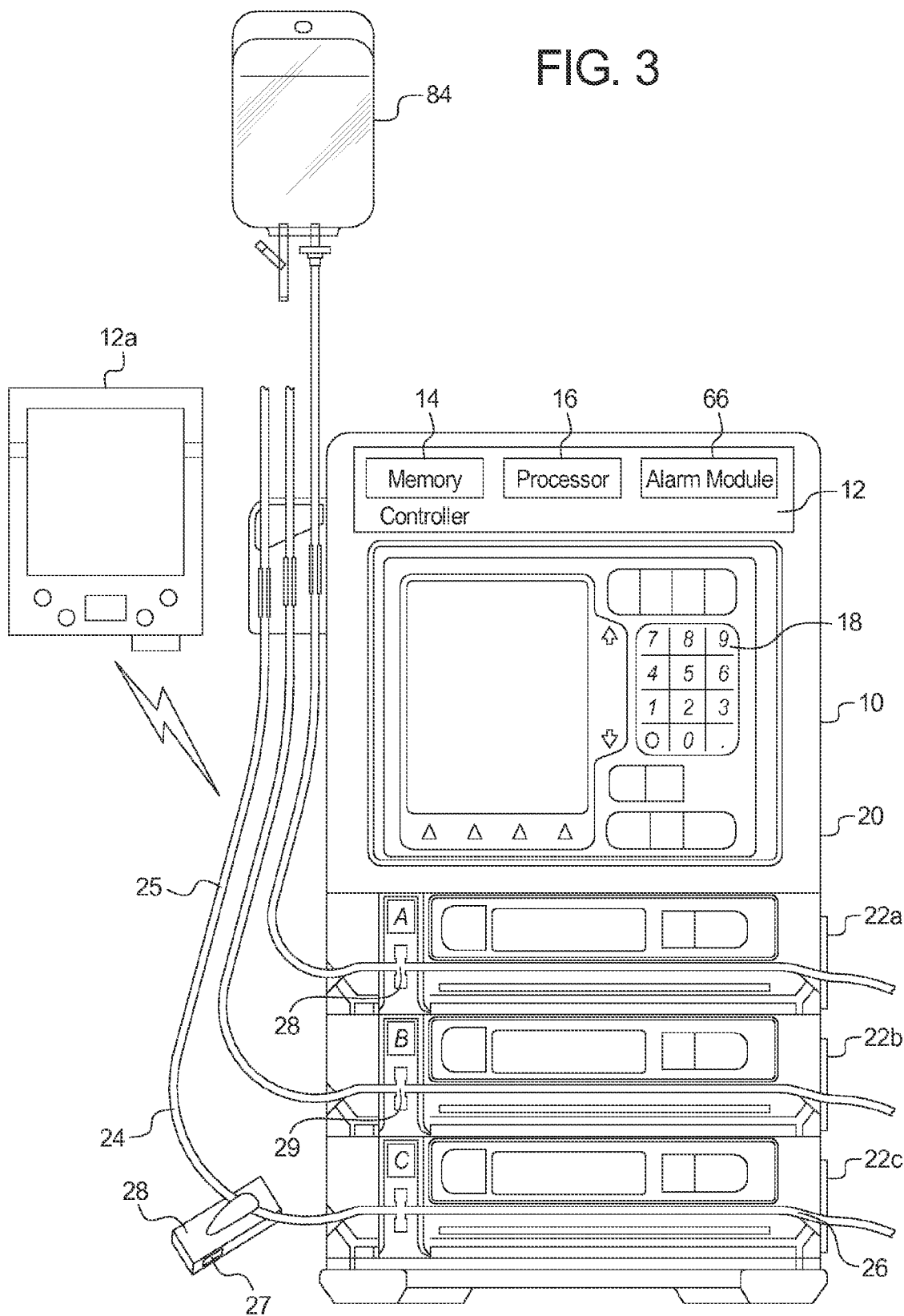
FIG. 3 is a front elevation view of one medical device and controller used in the system of the present disclosure.

FIG. 3 illustrates one embodiment of the medical device 10 of the present invention. In general, the system of the present invention incorporates a medication delivery device 10, a controller 12 having a memory 14, a processor 16 and an interface device 19. The interface device 19 may comprise one or both of an input device 18 and a display device 17. Further, the components of the interface device 19 (i.e., the input device 18 and the display device 17) may be separate components, or they may be integral components. As an example, the interface device 19 may be a touch screen which provides the function of a display device and an input device.

In one embodiment, the controller 12 is an internal component of the infusion pump 10. In an alternate embodiment, the controller 12a is a separate and distinct component from the infusion pump 10. As an example, the controller 12a may be a stand-alone personal digital assistant (PDA) controller 12a, also shown in FIG. 3, which is utilized for developing a medication therapy and subsequently transmitting signals to operate the medical device 10.

Typically, when the controller 12a is a separate and distinct component from the medical device 10, such as with a PDA, the controller 12a performs all of the processing of the program parameters, comparison of the program parameters with the preprogrammed medication therapies, developing of the medication therapies and scheduling of the medication therapies, and offering of medication therapies in response to entered patient and condition data. As an example, to operate the medical device 10 with a stand-alone controller 12a, the controller 12a may develop an output signal which is sent to the motor of the medical device 10. The level of the output signal, which may be a variable power signal, will determine the rate at which the motor operates to deliver medication to the patient.

One type of infusion pump that may be used in the present invention is that disclosed in U.S. Pat. No. 5,842,841, issued to Danby et al. and commonly assigned to the assignee of the present invention. As shown in FIG. 3, the infusion pump 10 has a housing 20, an input device and a plurality of pumping channels 22a, 22b, and 22c. In the present invention, each of the pumping channels will be independently programmable for delivering a variety of medication therapies to a particular patient. In operation, an operator, such as a nurse or other clinician, would commence infusion of a medicament by inserting the tubing 25 of a standard IV line set 24 into a tube loading orifice 26, or tubeway 26, located on the front of any of the housing channels. The line set 24 may include one or more of the following components: the IV tubing 25, a slide clamp 28, a connector, and a container 84. Additional or fewer components may make up the line set 24. Additionally, the operator would simultaneously insert a slide clamp 28 which is associated with the tube set 24 into an appropriate slide clamp orifice 29 located upstream, i.e., more toward the fluid source, of the tube loading orifice 26. The operator would then actuate a tube loading sequence in which a series of pawls and a moveable upper jaw would serve to seize the tube 25 of the line set 24 and draw it into a tubeway 26. As the loading cycle progresses, the jaws and pawls close about the tube 25 capturing the tube 25 within the tubeway 26. Sequentially, as the valves close to occlude the tube 25, the slide clamp 28 would be moved to a position such that the slide clamp 28 would no longer occlude the tube 25. Upon receipt of appropriate signals from an associated controller which would determine the pumping speed, allowable volume of air, temperature and pressure, the pump is actuated wherein fluid is drawn from the fluid source and expelled from the pump 10 according to the medication therapy. As explained in detail further herein, each of the process parameters and/or patient profiles necessary to develop a medication therapy, and potentially the entire medication therapy may be provided to the controller through an information identifier 27 found in connection with the line set 24. The information identifier 27 may be contained on any component of the line set 24, including but not limited to the tubing 25, the container 84 and the slide clamp 28.

As explained above, the system 30 of the present invention is utilized for programming a medical therapy in a medical device 10. The system 30 of the present invention can be implemented in software (e.g., firmware), hardware, or a combination thereof. In the currently contemplated best mode, the system 30 has a medical device operating system that is implemented in software, as an executable program. The medical device operating system may reside in, or have portions residing in, any computer, a server, the medical device 10 or a controller of a digital assistant 12*a*.

Generally, in terms of hardware architecture, as shown in FIG. 3, the controller 12 is a computer that includes a processor 16, a memory 14, and one or more input and/or output (I/O) devices 18 (or peripherals) that are communicatively coupled via a local interface. The local interface can be, for example, but not limited to, one or more buses or other wired or wireless connections, as is known in the art. The local interface may have additional elements, which are omitted for simplicity, such as additional controllers, buffers (caches), drivers, repeaters, and receivers, to enable communications. Further, the local interface may include address, control, and/or data connections to enable appropriate communications among the other computer components.

The processor 16 is a hardware device for executing software, particularly software stored in memory 14. The processor 16 can be any custom made or commercially available processor, a central processing unit (CPU), an auxiliary processor among several processors associated with the computer, a semiconductor based microprocessor (in the form of a microchip or chip set), a macroprocessor, or generally any device for executing software instructions. Examples of suitable commercially available microprocessors are as follows: a PA-RISC series microprocessor from Hewlett-Packard Company, an 80x86 or Pentium series microprocessor from Intel Corporation, a PowerPC microprocessor from IBM, a Sparc microprocessor from Sun Microsystems, Inc., or a 68xxx series microprocessor from Motorola Corporation.

The memory 14 can include any one or a combination of volatile memory elements (e.g., random access memory (RAM, such as DRAM, SRAM, SDRAM, etc.)) and nonvolatile memory elements (e.g., ROM, hard drive, tape, CDROM, etc.). Moreover, memory 14 may incorporate electronic, magnetic, optical, and/or other types of storage media. The memory 14 can have a distributed architecture where various components are situated remote from one another, but can be accessed by the processor 16.

The software in memory 14 may include one or more separate programs, each of which comprises an ordered listing of executable instructions for implementing logical functions. In the example of FIG. 3, the software in the memory 14 includes a suitable operating system (O/S). A non-exhaustive list of examples of suitable commercially available operating systems is as follows: (a) a Windows operating system available from Microsoft Corporation; (b) a Netware operating system available from Novell, Inc.; (c) a Macintosh operating system available from Apple Computer, Inc.; (d) a UNIX operating system, which is available for purchase from many vendors, such as the Hewlett-Packard Company, Sun Microsystems, Inc., and AT&T Corporation; (e) a LINUX operating system, which is freeware that is readily available on the Internet; (f) a run time Vxworks operating system from WindRiver Systems, Inc.; or (g) an appliance-based operating system, such as that implemented in handheld computers or personal digital assistants (PDAs) (e.g., PalmOS available from Palm Computing, Inc., and Windows CE available from Microsoft Corporation). The operating system essentially controls the execution of any other computer programs, and provides scheduling, input-output control, file and data management, memory management, and communication control and related services.

The medical device operating system may be a source program, executable program (object code), script, or any other entity comprising a set of instructions to be performed. When a source program, the program needs to be translated via a compiler, assembler, interpreter, or the like, which may or may not be included within the memory 14, so as to operate properly in connection with the O/S. Furthermore, the medical device operating system can be written as (a) an object oriented programming language, which has classes of data and methods, or (b) a procedure programming language, which has routines, subroutines, and/or functions, for example but not limited to, C, C++, Pascal, Basic, Fortran, Cobol, Perl, Java, and Ada. In one embodiment, the medical device operating system is written in C++. In other embodiments the medical device operating system is created using Power Builder. The I/O devices 18 may include input devices, for example but not limited to, a keyboard, mouse, scanner, microphone, touch screens, interfaces for various medical devices, bar code readers, stylus, laser readers, radio-frequency device readers, etc. Furthermore, the I/O devices 18 may also include output devices, for example but not limited to, a printer, bar code printers, displays, etc. Finally, the I/O devices 18 may further include devices that communicate both inputs and outputs, for instance but not limited to, a modulator/demodulator (modem; for accessing another device, system, or network), a radio frequency (RF) or other transceiver, a telephonic interface, a bridge, a router, etc.

When the medical device operating system is implemented in software, it should be noted that the medical device operating system can be stored on any computer readable medium for use by or in connection with any computer related system or method. In the context of this document, a computer readable medium is an electronic, magnetic, optical, or other physical device or means that can contain or store a computer program for use by or in connection with a computer related system or method. The medical device operating system can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the instruction execution system, apparatus, or device. The computer readable medium can be for example, but not limited to, an electronic, magnetic, optical, electromagnetic, infrared, or semiconductor system, apparatus, device, or propagation medium. More specific examples (a non-exhaustive list) of the computer-readable medium would include the following: an electrical connection (electronic) having one or more wires, a portable computer diskette (magnetic), a random access memory (RAM) (electronic), a read-only memory (ROM) (electronic), an erasable programmable read-only memory (EPROM, EEPROM, or Flash memory) (electronic), an optical fiber (optical), and a portable compact disc read-only memory (CDROM) (optical). Note that the computer-readable medium could even be paper or another suitable medium upon which the program is printed, as the program can be electronically captured, via, for instance, optical scanning of the paper or other medium, then compiled, interpreted or otherwise processed in a suitable manner if necessary, and then stored in a computer memory.

In another embodiment, where the medical device operating system is implemented in hardware, the medical device operating system can be implemented with any or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

Figure 4:
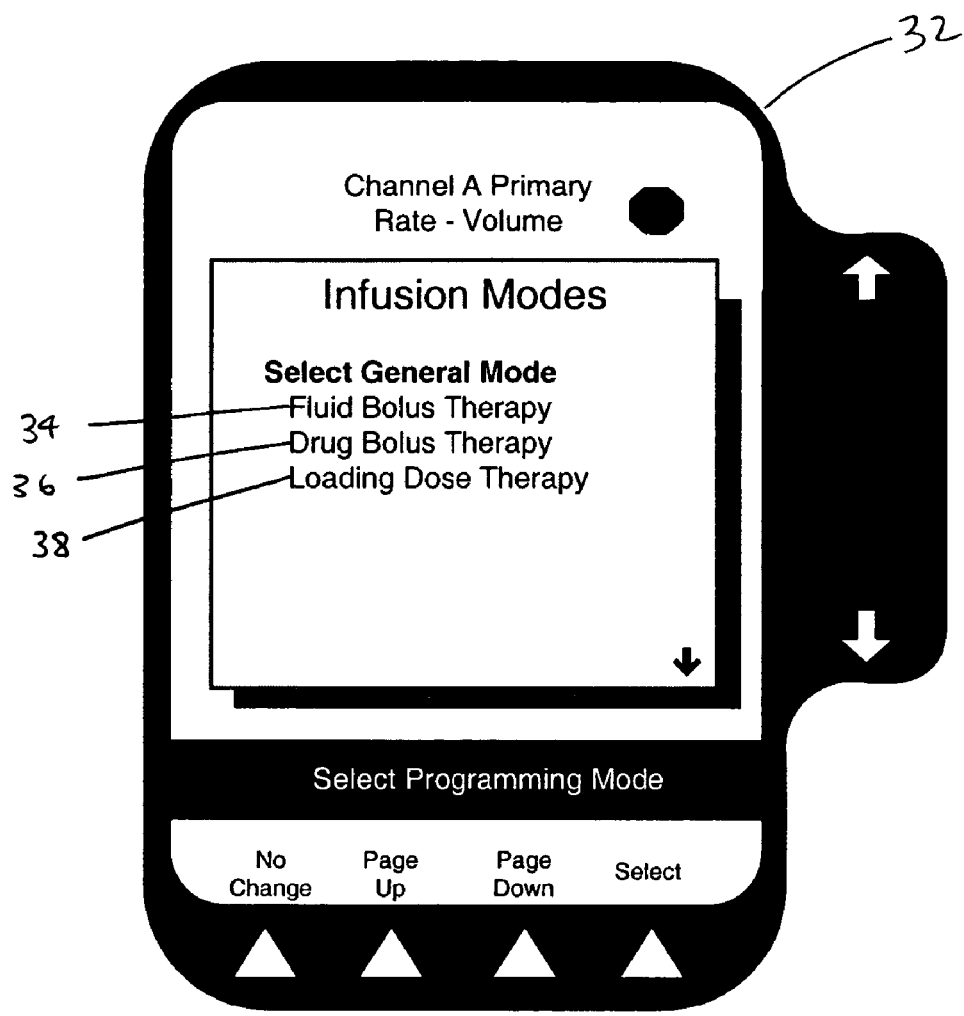
FIG. 4 is a depiction of a therapy selection interface screen of the system of the present disclosure.

Returning back to FIG. 1, the flowchart shown depicts one embodiment of a system 30 for programming a medical device 10 of the present invention. The first step in the programming process is to initiate a start command, shown at step 31 in FIG. 1. The start command 31 typically incorporates turning on the controller 12 of either the infusion pump 10 or a separate controller 12a. After the start command has been initiated, an infusion selection screen 32 appears. One depiction of an infusion selection screen 32 is illustrated in FIG. 4. As shown, the infusion selection screen 32 is adapted to allow the operator the ability to select an infusion therapy. In one embodiment, the available infusion therapies for selection are a fluid bolus infusion therapy 34, typically utilized for the programming of a non-drug bolus medication delivery, a drug bolus infusion therapy 36, and a loading dose infusion therapy 38. A bolus is typically defined as a relatively large volume of fluid or dose of a drug or test substance given via an intravenous, epidural, subcutaneous or arterial route, often rapidly, to hasten or magnify a response. A loading dose is typically defined as a volume of fluid or dose of a drug or test substance given via an intravenous, epidural, subcutaneous or arterial route, prior to a maintenance infusion of that same fluid, drug or test substance. One purpose of a bolus or a loading dose is to achieve rapid serum concentration. This, however, may increase the risk of adverse effects. Accordingly, means to reduce the possibility of increased risk are sought. As explained above, this disclosure seeks to provide, among other things, means to reduce the risk of error when providing a medication, whether a drug or a non-drug, to a patient.

As an aspect of the invention, the memory 14 is preloaded with medication therapies. The type of medication therapies that are preloaded in the memory 14 includes at least one of bolus dose medication therapies, both for drug boluses and for non-drug boluses, loading dose medication therapies, and standard infusion therapies. The preloaded medication therapies may identify acceptable ranges and/or limits for each of the process or program parameters required to develop a particular medication therapy. This allows a hospital to establish a standard bolus dose or loading dose for each medication, both drug and non-drug, that is defined in the library of memory 14. This also allows a hospital to establish a standard loading dose or bolus dose therapy for various patient condition profiles. As one of ordinary skill in the art understands, an acceptable range and/or limit for a particular program parameter may be adjusted based on the other program parameters. For example, if the infusion time increases, the allowable range/limit for the infusion dose may increase, whereas if the infusion time decreases, the allowable range/limit for the infusion dose may decrease. Additionally, the allowable rate for a particular medication may change depending on the concentration of the medication. Numerous other examples are possible.

After the operator selects the appropriate infusion therapy at the infusion selection screen 32, the system provides the operator the ability to enter programming parameters at step 40 (see FIG. 1) for the delivery of the medication. The program parameters vary depending on type of infusion, type of parameters set for request by the hospital or other caregiver setup, medication, etc. Generally, the program parameters are the information and/or instruction set that is necessary to program a medical device to operate in accordance with an order or prescription. Various program parameters for a bolus dose medication therapy comprise at least medication type, medication concentration, medication amount, individual bolus volume, total bolus volume, bolus rate, timing between bolus deliveries, maximum number of boluses, maximum number of boluses per unit time, and patient weight. Similarly, various program parameters for a loading dose medication therapy comprise at least medication type, medication concentration, medication amount, loading dose volume, loading dose rate, loading dose time, maintenance rate, maintenance volume, maintenance time, diluent volume and patient weight. One of ordinary skill in the art will appreciate that additional program parameters are possible for these and other infusion therapies.

Figure 5:
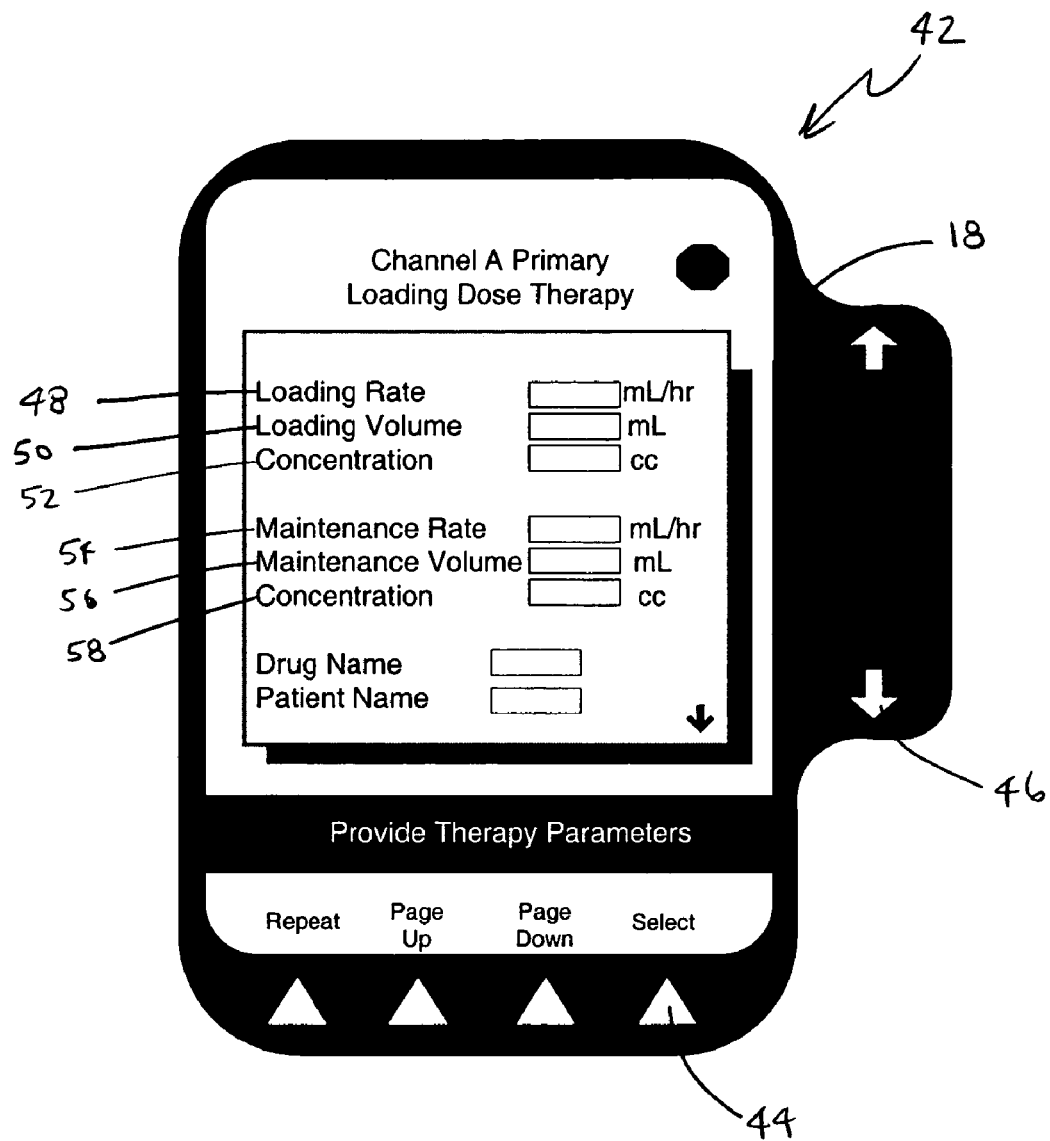
FIG. 5 is a depiction of a data entry screen of the system of the present disclosure.

In one embodiment of the present invention, after the operator has made a selection of the medication therapy type at step 32, the system will provide an input screen that only allows for receiving program parameters relevant to the received medication therapy type. For example, if a bolus dose medication therapy were selected at step 32, the system would only provide for input of those program parameters relevant to a bolus dose medication therapy. Similarly, if a loading dose medication therapy were selected at step 32, the system would only provide for input of those program parameters relevant to a loading dose medication therapy. One depiction of a program parameter entry screen 42 for a loading dose therapy is illustrated in FIG. 5. As shown for exemplar purposes, the loading dose parameter entry screen 42 requests data on loading rate 48, loading volume 50, concentration 52, maintenance rate 54, maintenance volume 56 and concentration 58.

The program parameter entry screen shot 42 illustrated in FIG. 5 is also an example of an interface device 19 that operates as an input device 18 and a display device 17. Program parameters are able to be programmed through the use of selection keys 44 and up/down arrows 46, and the display is provided via the video screen.

Additionally, in one embodiment of the present invention, after the operator has made a selection of the medication therapy type at step 32, and after the medication type has been provided to the controller 12, the system 30 may provide a suggested medication therapy for the selected medication therapy type and medication type. Thus, instead of, or in conjunction with displaying the program parameters relevant to the specific medication therapy type selected, the system 30 may provide an identification of the program parameters and the values therefor, for the relevant parameters for that medication therapy type. As an example, if a specific narcotic drug was selected, and at step 32 the operator selected to provide this narcotic via a bolus therapy, the system 30 will identify a suggested medication therapy for that medication and for that type of medication therapy. The operator will then be able to accept of modify any or the parameters at step 60.

Referring back to FIG. 1, at step 60, after the operator has entered or modified the program parameters into the input device 18, the processor 16 receives the parameters and compares the received program parameters to the preloaded medication therapies. In a preferred embodiment, this may incorporate the use of an algorithm in the processor 16 to determine the appropriate ranges for each parameter, possibly based on a preprogrammed sliding-scale matrix.

At step 62, after the processor 16 compares the received program parameters to the preloaded medication therapies in the memory 14, the processor 16 determines if the received program parameters exceed the preprogrammed acceptable ranges for each of the process or program parameters of the particular medication therapy. If the received program parameters comport with the preloaded medication therapies, the processor 16 may at this time develop at least a part of the medication therapy based on the received process parameters.

Figure 7:
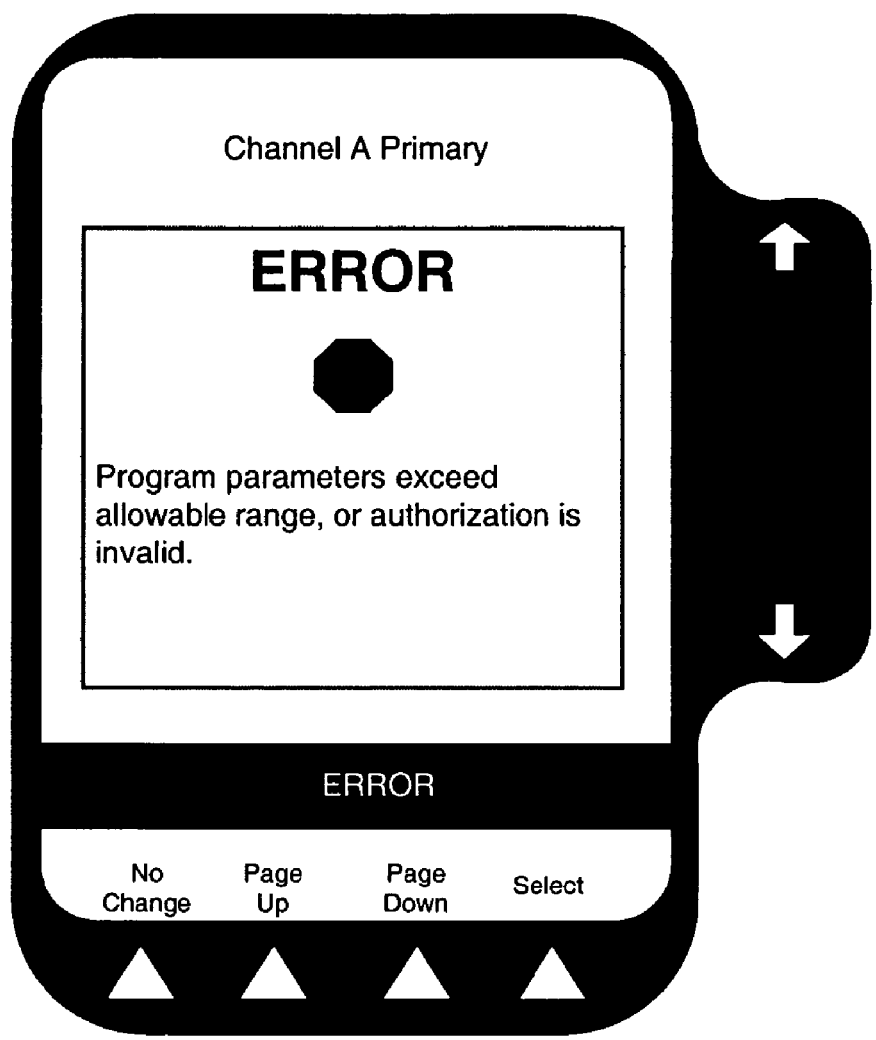
FIG. 7 is a depiction of another embodiment of an alarm screen of the system of the present disclosure.
Figure 8:
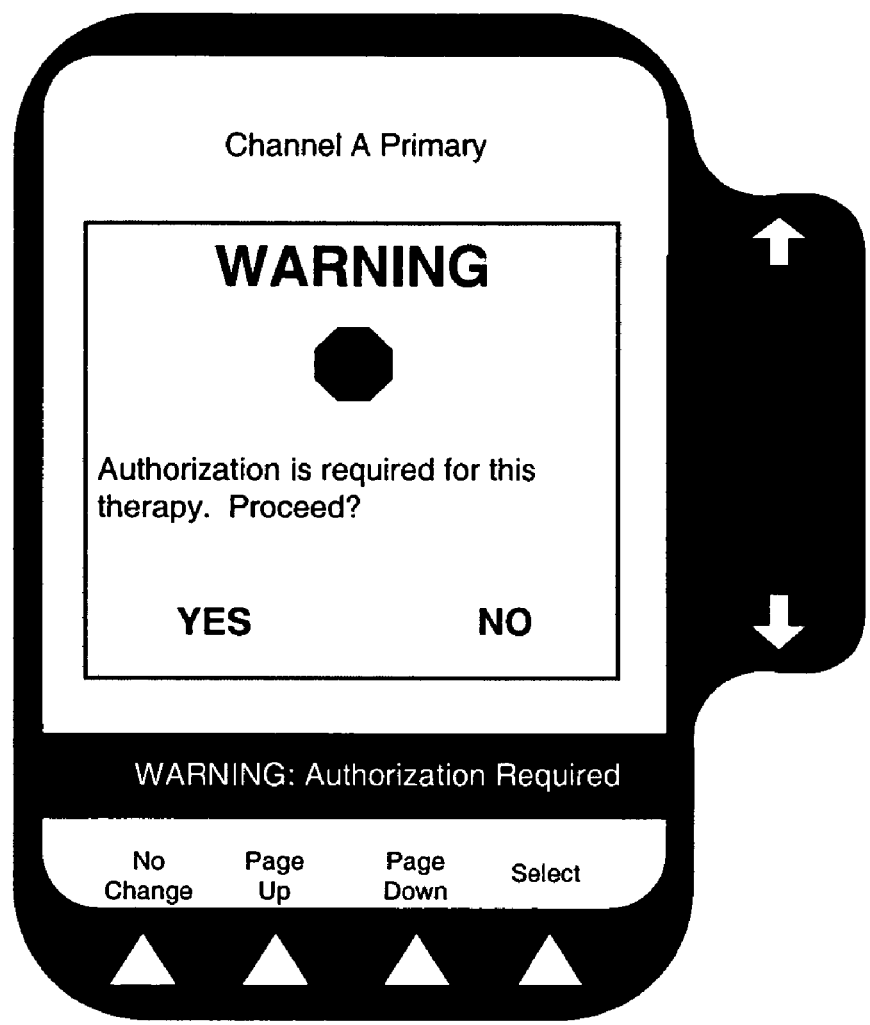
FIG. 8 is a depiction of an authorization screen of the system of the present disclosure.

If, however, any of the program parameters for the particular medication therapy exceed the limits set in the preloaded medication therapies, the system provides an alarm or notification at step 64 to alert the clinician that the dose is outside the hospital formulary's recommended range. The alarm may be provided by an alarm module 66 which is a component of the controller 12 as illustrated in the embodiment illustrated in FIG. 3. The alarm may be a visual or an audible alarm, and different alarm types may have different visible or audible alerts. Further, as shown in step 68 in the flowchart of FIG. 1, the alarm may be a hard alarm or a soft alarm. When the parameter limits are not allowed to be exceeded, a hard alarm is provided to alert the operator that a program parameter is invalid and that they must modify at least one of the program parameters. One depiction of a hard alarm is provided in FIG. 7. After receiving a hard alarm the operator has the option to modify one or more of the program parameters at step 69. If the operator does not modify at least one of the program parameters to remove the hard alarm, the therapy request will be denied in step 70. If the operator does modify at least one of the program parameters, the system will revert back to step 60 of FIG. 1 to determine if the revised parameters are within the preprogrammed acceptable ranges.

Figure 6:
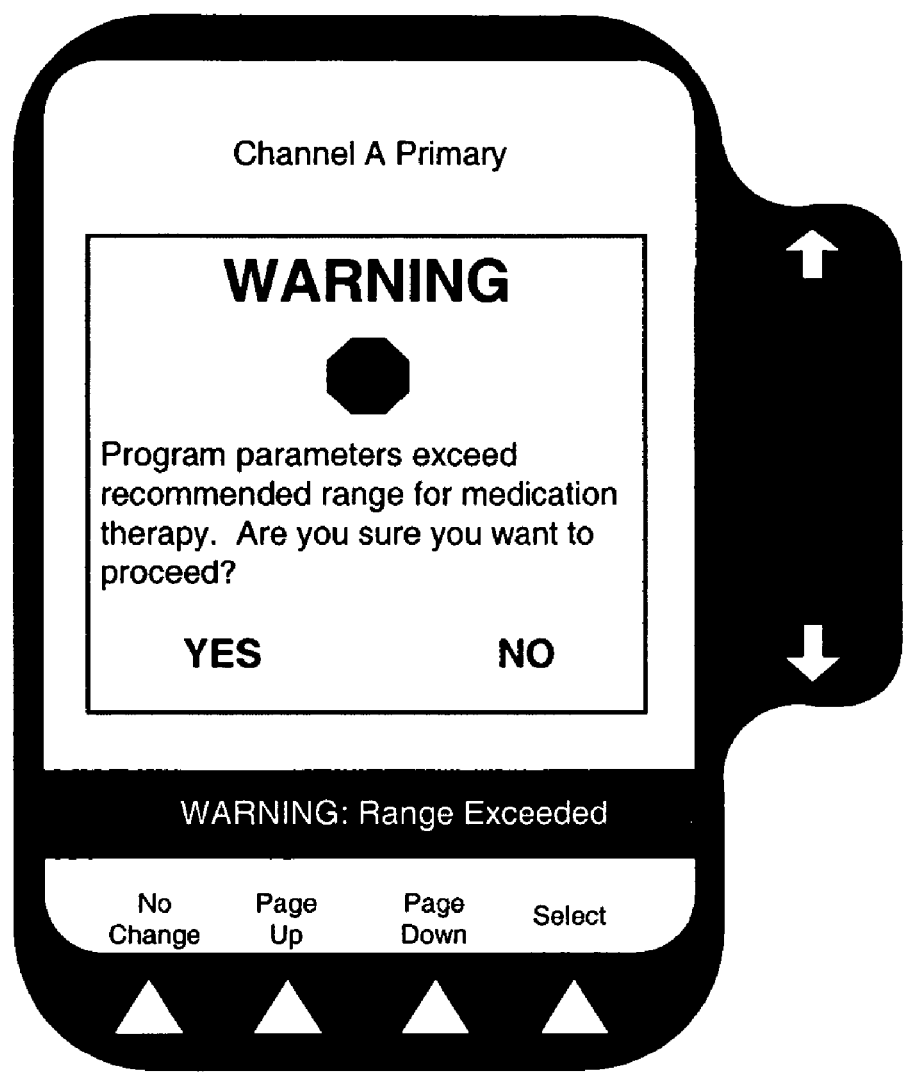
FIG. 6 is a depiction of one embodiment of an alarm screen of the system of the present disclosure.

As opposed to a hard alarm, a soft alarm allows the parameter limits to be exceeded without modifying the out-of-limit parameter. The soft alert does, however, provided a notification to the operator that at least one of the program parameters exceeds a limit set in the preloaded medication therapy. A screen shot for one embodiment of a soft alarm is depicted in FIG. 6. Following the receipt of a soft alarm, a request is made to provide the override at step 72 in FIG. 1. The operator can provide the override response in an interface module of the input device 18. As explained above, the interface module may comprise a touch screen, keyboard, mouse, etc. If the request is answered in the negative, then an override is not provided for a soft alarm and the therapy request will be denied in step 70. Further, the programming sequence will be terminated at step 80. If the request is answered affirmatively, however, the system proceeds to step 74 to determine if authorization is required.

As shown in FIG. 1, another means by which an operator may arrive at step 74 occurs when the received program parameters, entered at step 40, are determined at steps 60 and 62 to be within the preprogrammed limits or ranges.

At step 74 the processor determines if authorization to proceed is required. There are several processes by which authorization may be required. First, if a soft alarm has been overridden then authorization is required. Second, if a two-signature medication, such as a narcotic or a blood, is provided, an authorization is required. It is understood that additional processes exist which require authorization.

Accordingly, if it is determined that authorization is required because a soft alarm has been overridden, but dual signatures are not required, the system proceeds past step 75 to step 77. At step 77 an alarm/notification is provided alerting the operator that authorization is required to proceed. At step 79, authorization to proceed due to a parameter override is either provided or it is not provided. If authorization to override the program parameter is not provided at step 79, then the system proceeds to step 70 and the programming therapy request is denied. If authorization to override the program parameter is provided at step 79, then the system proceeds to step 81. At step 81, the pharmacy and the treating physician are notified that the delivery parameters set for therapy are out of the hospital's formulary range.

If it is determined at steps 74 and 75 that authorization is required because either a soft alarm has been overridden or that dual signatures are required, the system proceeds to step 76. At step 76 the system provides an alarm/notification that two signatures/authorizations are required. Then at step 78 the system determines whether the two authorization signatures have been provided. If the two authorization signatures are not provided, the system proceeds to step 70 and the programming therapy request is denied. If the two authorization signatures, which may be a secure authorization such as the entry of an authorization code, are provided at step 78, the system proceeds to step 81. If the delivery parameters were overridden at step 72, then at step 81 the pharmacy and the treating physician are notified that the delivery parameters set for therapy are out of the hospital's formulary range. If the delivery parameters were not overridden at step 72, then no notification to the treating physician and pharmacy is necessary.

Once the appropriate authorization(s) have been provided at steps 78 and 79, or if authorization is not required at step 74, the system proceeds to step 82 of FIG. 1. At step 82, the system requests the operator to select the appropriate pumping channel and identify the appropriate container and line set 24, if such has not been done yet. Recognition of the line set in the pumping channel may occur manually by the operator entering information relating to the container 84, medication in the container 84, and channel 22 in which the tubing 25 is located, or the recognition may occur automatically. It is also understood that recognition of the container 84 and line set 24 may occur much earlier in the programming sequence.

Figure 9:
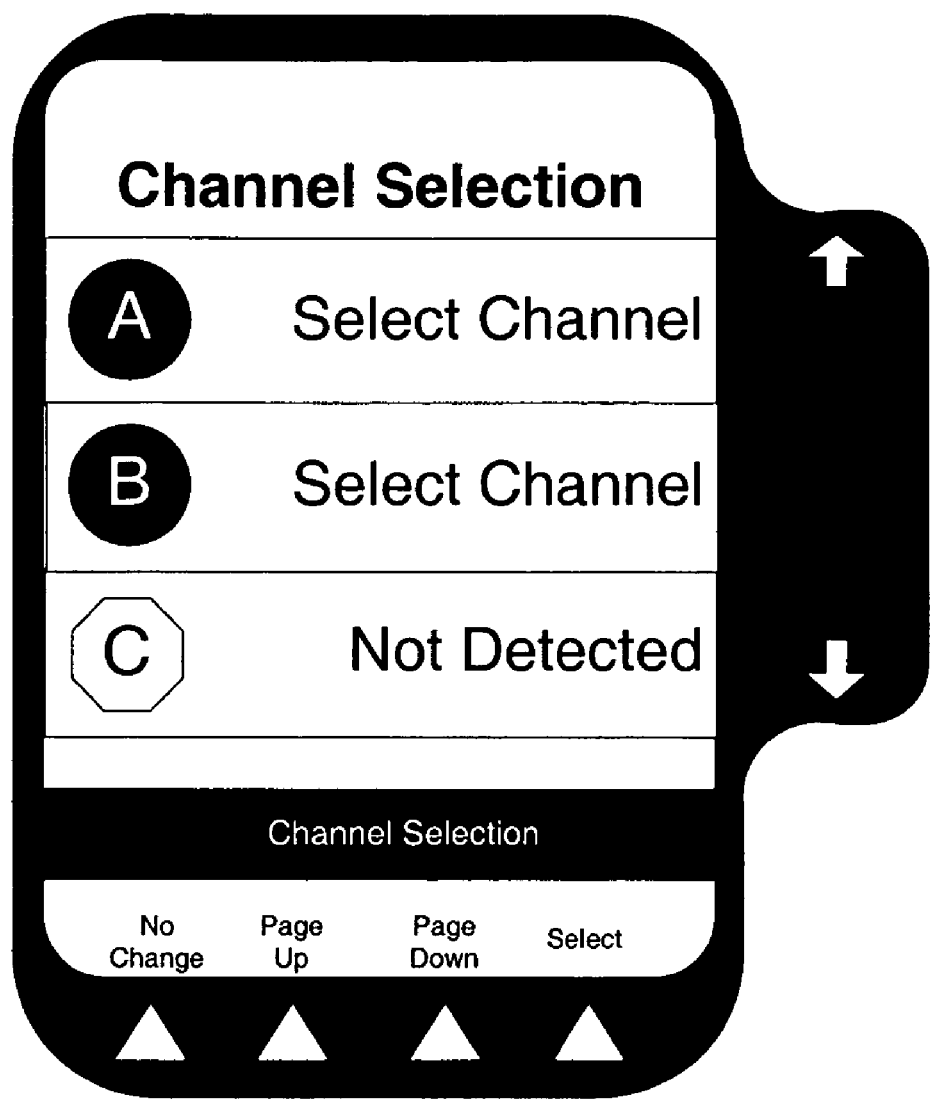
FIG. 9 is a depiction of a channel selection screen of the present disclosure.

For reference, FIG. 9 depicts a channel selection screen of the controller 12. In the routine depicted in FIG. 9, the operator identifies the appropriate channel for the programmed infusion therapy. If the container, line set, channel recognition and/or parameter programming is not to be performed manually, one means for providing automatic recognition/programming is with the use of an information identifier 27 on a component of the line set 24. The information identifier 27 may contain information concerning: the patient, such as the patient name, age, sex, weight, allergies, condition, etc.; the medicine connected as part of the line set 24 (i.e., in the container 84), such as the drug/non-drug type, name, concentration, etc.; and, the medication therapy to be conducted with the line set, including all or any of the process parameters necessary for the medication therapy. Such process parameters may include at least medication type, medication concentration, medication amount, individual bolus volume, total bolus volume, bolus rate, dose, timing between bolus deliveries, maximum number of boluses, maximum number of boluses per unit time, loading dose volume, loading dose rate, loading dose time, maintenance rate, maintenance volume, maintenance time, maintenance dose, diluent volume and patient weight. Finally, the information identifier 27 may include information concerning profile data, including but not limited to patient profiles data such as patient pain state, chronologic age, age group, and gestational age, and condition profile data such as the medical condition or medical disease state, including but not limited to renal disease, congenital heart disease, and liver failure. In addition to including specific medication therapy information, the information identifier 27 may also include generic medication therapy. For example, the information identifier 27 may include process parameters and data applicable to a variety of medications, a category of medications, or to a category of patient and/or condition profiles.

The information identifier 27 may be attached to the line set 24 by the manufacturer of the line set 24, by the hospital pharmacy, or by some other entity. When the information identifier 27 is attached to the line set 24 by the manufacturer, the line set typically does not yet include a medication container 84. As such, the line set 24 with the information identifier 27 may be pre-made and provided as having information applicable to a category or group of medications. This line set 24, with the information identifier 27, may then be attached to a container 84 having medication within this category. Alternatively, the line set 24 may be highly customized and contain many of the patient specific and/or therapy specific process parameters identified above. Such customization is typically performed by a pharmacy wherein a specific prescription and therapy instructions are added to the identification identifier 27.

Data from the information identifier 27 is transferred to the controller 12 just as if it were input into a keyboard of the input device 18. In one embodiment, the slide clamp 28 has one or more of machine readable indicia, a barcode and/or a radio frequency transmitter, including RFID, which communicates with the controller 12 to transmit the information to the controller 12. In a similar embodiment, the controller 12 may have as an input device 18 a barcode reader, a radio frequency receiver, a fiber optic receiver, a laser readable receiver and/or an infrared receiver etc. to receive the information from the information identifier 27.

When any information is to be received by the input device 18 of the controller 12 via a line set information identifier 27, it is understood that it may be beneficial when this information is transferred to the controller early in the programming process, and preferably at step 40 as seen in FIGS. 1 and 2.

Figure 10:
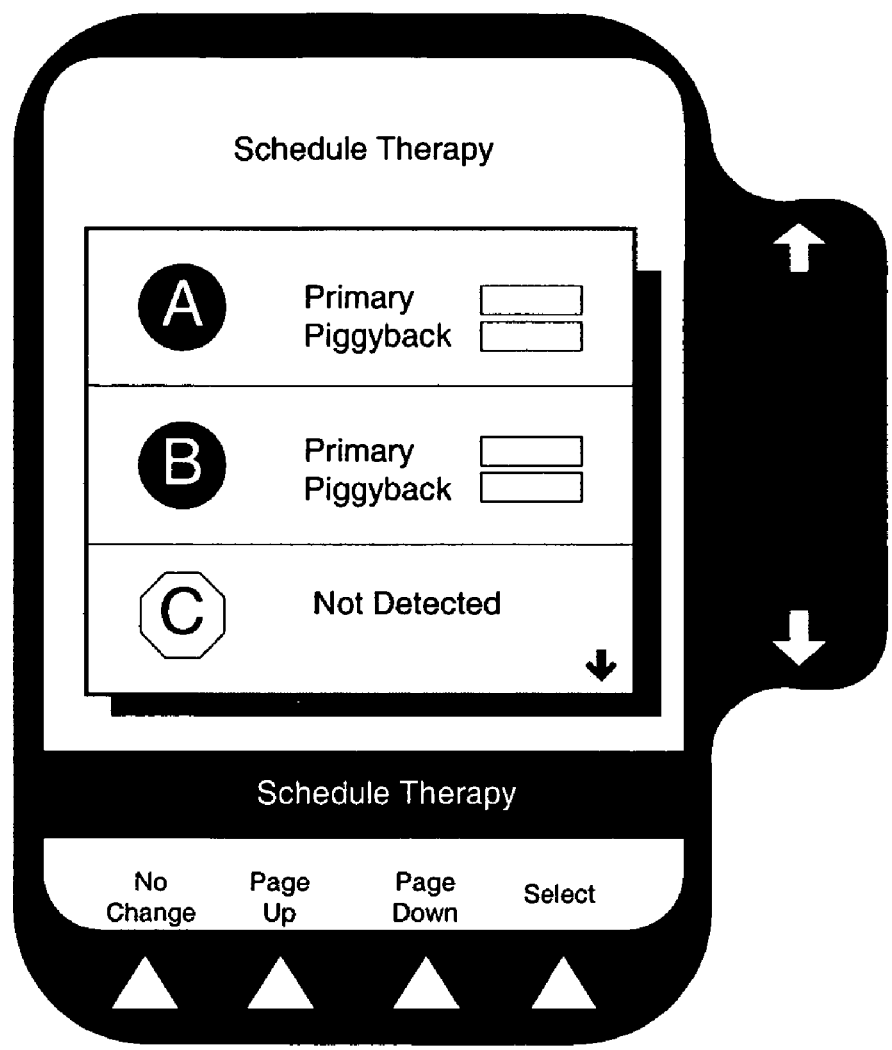
FIG. 10 is a depiction of a scheduling screen of the system of the present disclosure.

After the channel 22 has been selected in step 82, and the container 84, including the medication and line set 24, have been identified, the processor 16 of the system 30 queries the operator to develop a schedule for the medication therapy in step 86. One component of the schedule query is to identify the therapy as the primary therapy, or as a piggyback therapy as depicted in FIG. 10. With a three-channel multi-channel infusion pump, the possible medication therapies include at least a primary medication therapy, a first piggyback medication therapy and a subsequent piggyback medication therapy. In such a configuration the primary medication therapy is delivered first (i.e., a first medication therapy), the first piggyback medication therapy is delivered second (i.e., a second medication therapy), and the subsequent piggyback medication therapy is delivered third (i.e., a third medication therapy). All of the medication therapies may be any of a standard medication therapy, a bolus dose medication therapy and/or a loading dose medication therapy.

Another component of the schedule query is the time and date of the delivery of the medication therapy. The controller 12 may be programmed in advance of either or both the delivery of the medication, and the attachment of the container 84 and line set 24 to the medical device 10.

As an example of a multi-container 84 and multi-channel program, the controller 12 may be programmed to provide a loading dose medication therapy from a primary container associated with the first pumping channel 22a, and follow the loading dose medication therapy with a maintenance medication therapy (i.e., a piggyback medication regimen) from either a second container associated with the second pumping channel 22b, or the same container on the first pumping channel 22a. Additionally, a subsequent piggyback medication therapy to the first two medications described above may be a bolus dose medication therapy from a third container connected to the third pumping channel 22c. Numerous other examples exist.

With the use of piggyback medication therapies, the system allows for the creation of first medication therapies (i.e., primary medication therapies), second medication therapies (i.e., piggyback therapies), third medication therapies (i.e., subsequent piggyback therapies), etc. The piggyback therapies are programmed following the same steps and with the same system 30, including all alarms and overrides identified above.

As an additional feature, the system may incorporate a repeat feature which allows the operator the ability to repeat any portion of program parameters, or an entire therapy without having to re-enter the parameters.

Referring now to FIG. 2, another system 30a is shown for programming a medical device 10 of the present invention. The first step in the programming process of system 30a is to initiate the start command at the controller (either a controller 12 connected to a medical device 10 or a stand-alone controller 12a), shown at step 31 in FIG. 2. After the start command has been initiated, the operator may select to proceed to the infusion selection screen 32. As explained above, the infusion selection screen 32, depicted in FIG. 4, allows the operator the ability to select an infusion therapy. If the operator selects an infusion therapy, the medication therapy provided as a result of the system 30a, fully described below, will operate under infusion delivery parameters for that specific infusion therapy. Specifically, as an example, if the operator selects a bolus dose medication therapy at step 32, the processor 16 will process the received profile data and provide as output one of the preloaded bolus medication therapies based on the processed profile data. Alternatively, the operator may skip step 32 and proceed directly to steps 90 and 91, depicted in FIG. 11, wherein the operator may enter profile data into the input device 18 comprising at least one of a patient profile 92, a condition profile 94 and a medication profile 96.

Profile data for the patient profiles 92 may comprise at least one of a patient pain state, a chronologic age, an age group, and a gestational age. Profile data for the condition profiles 94 may comprise at least one of a medical condition or medical disease state, such as renal disease, congenital heart disease, and liver failure. Finally, profile data for the medication profile 96 may include any data on the medication (i.e., drug, non-drug or diluent), including the name or type of medication to be delivered to the patient. Each one of the patient profile 92, condition profile 94 and medication profile 96 resides in the memory 14. More specifically, in addition to the medication therapies that are preloaded in the memory 14 as described above, the memory 14 is also preloaded with the patient profiles 92, condition profiles 94 and medication profiles 96 corresponding to a particular medication therapy.

Figure 11:
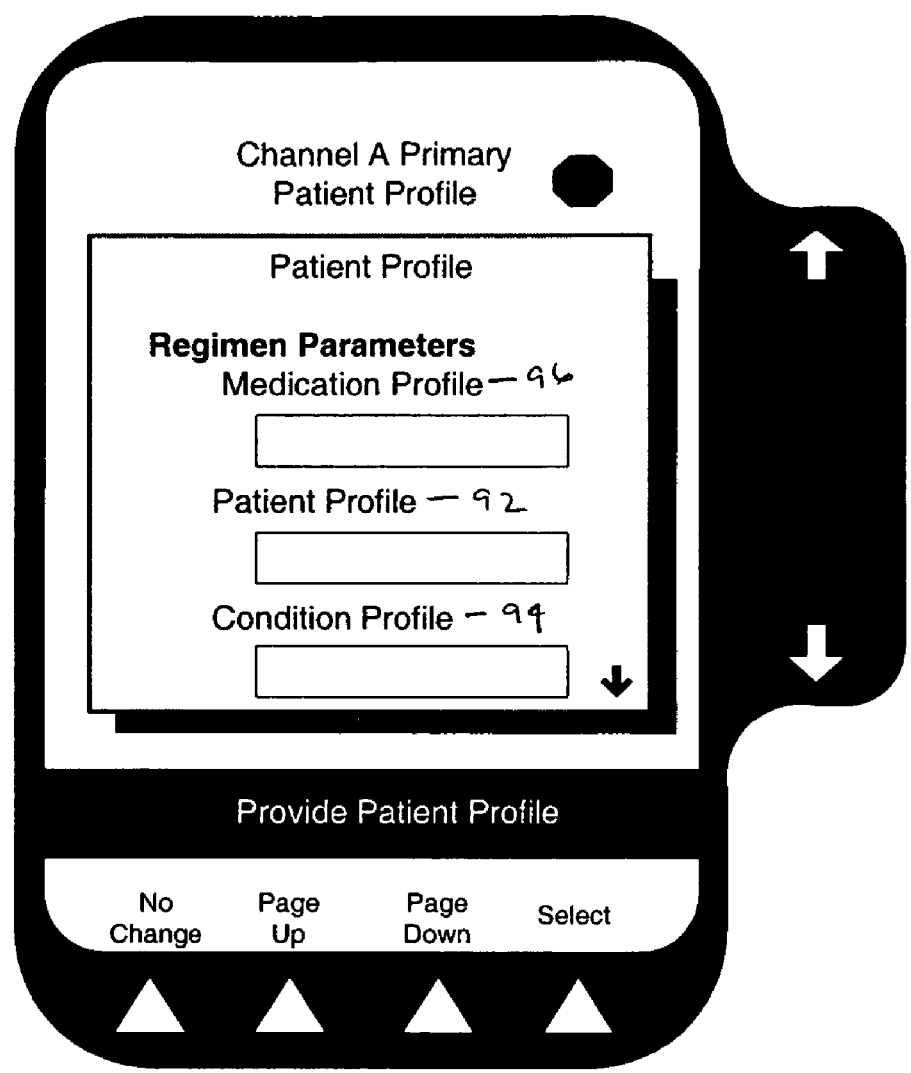
FIG. 11 is a depiction of one embodiment of a profile data entry screen of the system of the present disclosure.
Figure 12:
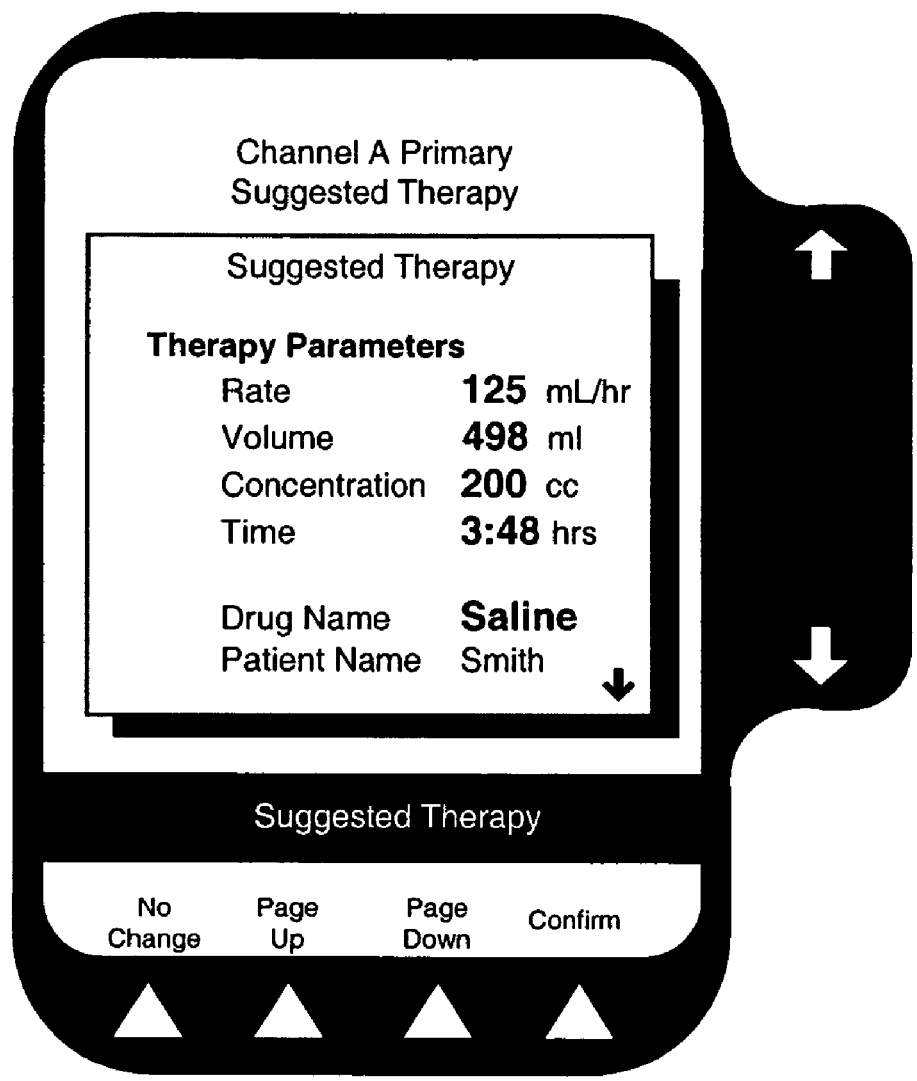
FIG. 12 is a depiction of suggested therapy screen of the system of the present disclosure.

After the operator enters the profile data, which may include manipulating drop-down selection menus in FIG. 11 (i.e., the input device 18), at steps 98 and 100, the profile data received by the input device 18 will be reviewed by the processor 16 and compared to data in the preloaded profiles 92,94,96 to determine the appropriate medication therapy. In one embodiment, the processor 16 has an algorithm that compares the received profile data to the preloaded profiles to provide the medication therapy. Finally, at step 102 the processor 16 will provide as output a medication therapy. The processor 16 typically selects the medication therapy from the preloaded medication therapies corresponding to the preloaded profiles 90-92 that further correspond to the received profile data. The medication therapy provided by the processor 16 typically comprises a medication type and delivery parameters. The delivery parameters comprise at least one of a dose, a rate and a concentration. An example of an output medication therapy is depicted in FIG. 12. In this example, the medication therapy includes the rate, volume, concentration, time and medication name.

Alternatively, if the output is provided as a bolus medication therapy, the delivery parameters may comprise at least one of a medication type, a medication concentration, a medication amount, an individual bolus volume, a total bolus volume, a bolus rate and a timing between bolus deliveries. And, if the output is provided as a loading dose medication therapy, the delivery parameters may comprise at least one of a medication type, a medication concentration, a loading dose volume, a loading dose rate, a loading dose time, a maintenance volume, a maintenance time and a diluent volume.

While the system 30a may provide a suggested medication therapy based solely on one profile data entry, if the operator enters more than one profile data in the input device 18 at steps 90, 92, shown in FIG. 11, such as entering data for both a patient profile and a condition profile, the processor 16 will perform a cross analysis to either obtain or develop a suggested medication therapy based on the pre-programmed medication therapies.

After the system 30a has provided a recommended medication therapy at step 102, the operator has the ability to accept or reject the recommended medication therapy at step 104. If the operator approves the recommended medication therapy at step 104, the system 30a proceeds to step 74, identified above, and the system proceeds as identified above. Conversely, if the operator rejects the recommended medication therapy at step 104, then the operator is provided the opportunity to adjust any of the parameters of the recommended medication therapy at step 106. If the operator chooses not to adjust any of the parameters at step 106, and the operator also chooses not to accept the recommended medication therapy, then the system 30a proceeds to the end and denies the therapy request. Alternatively, if the operator chooses to adjust any of the program parameters at step 106, the system 30a proceeds to step 62. As explained above, at step 62 the processor 16 will provide an analysis to determine if the program parameters meet the preprogrammed parameter ranges. Following step 62 the system 30a proceeds as explained above with respect to system 30.

Figure 13:
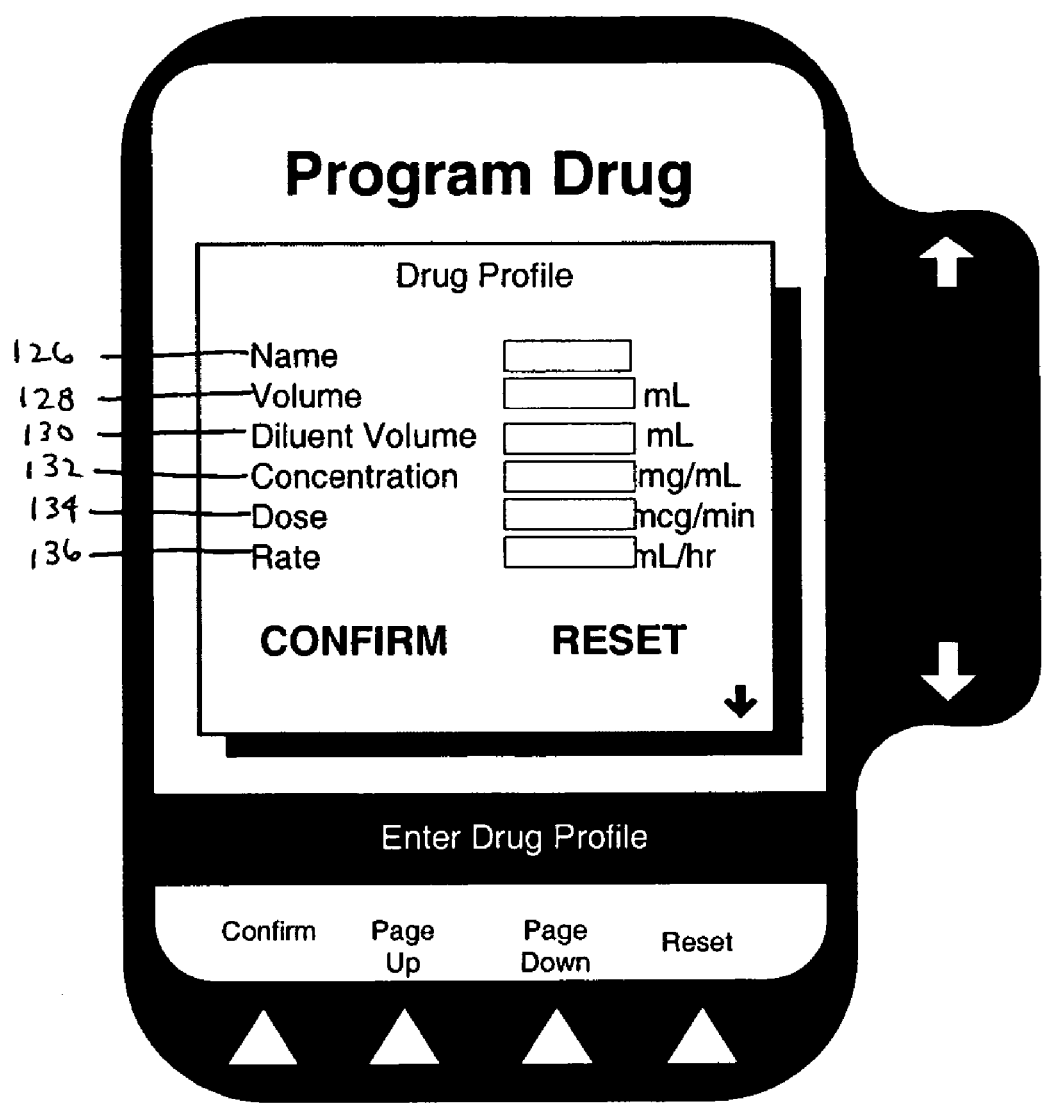
FIG. 13 is a depiction of a pre-programming screen of the system of the present disclosure.
Figure 15:
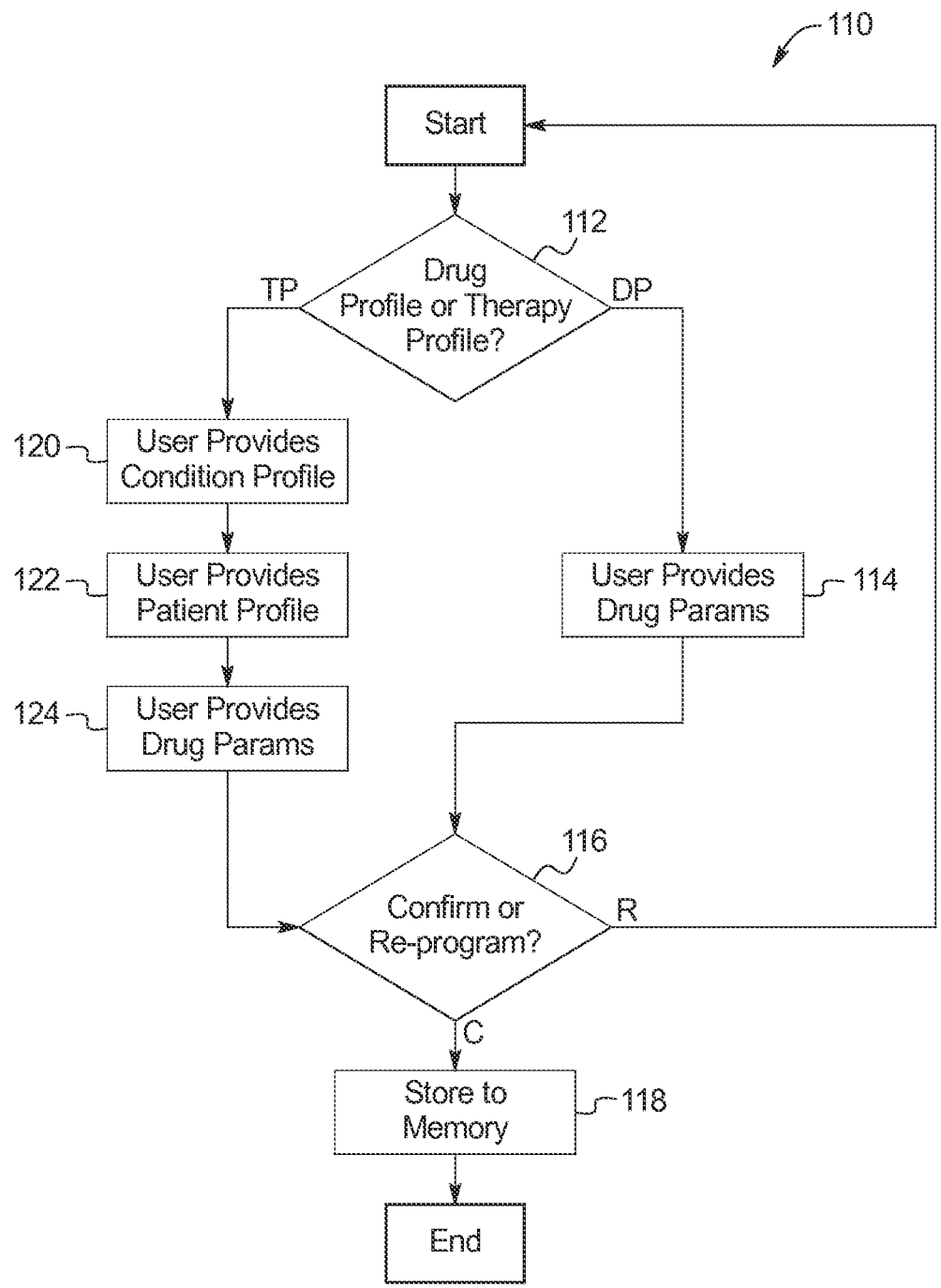
FIG. 15 is a flowchart depicting the pre-programming of a controller of the system of the present disclosure.

Referring now to the flowchart of FIG. 15. This flowchart depicts a system 110 whereby the controller 12 is pre-programmed, which is typically accomplished prior to programming of the medication therapy as identified in systems 30 and 30a above. As shown in FIG. 15, the first step in programming the controller 12 is to select, at step 112, whether the programming will be for a drug profile or for a medication therapy. A screen depiction for programming a drug profile is provided in FIG. 13. As shown, the programmer enters a variety of program parameters, at least some of which comprise the drug name 126, volume of infusion for the therapy 128, diluent volume for the therapy 130, concentration 132, dose 134 and rate 136. Additional program parameters are possible as understood by one of ordinary skill in the art.

Figure 14:
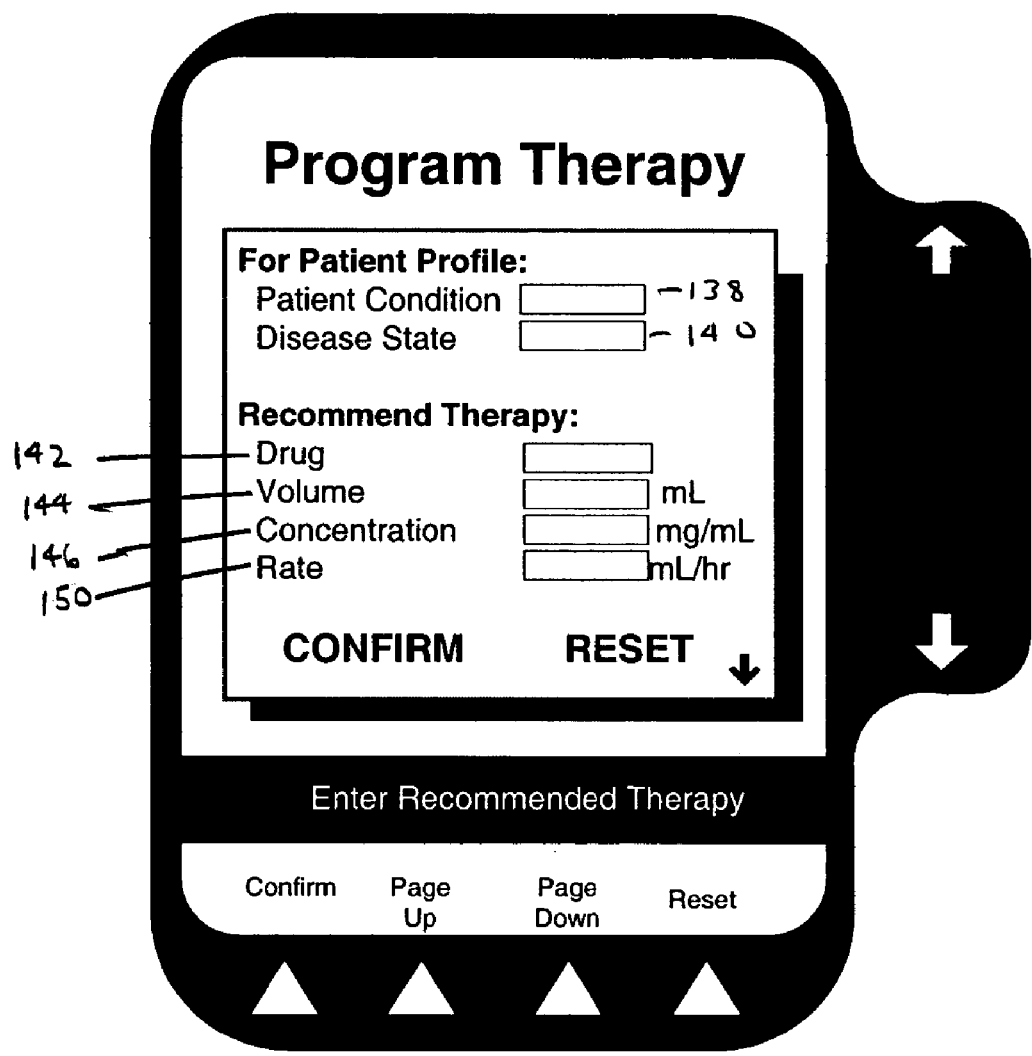
FIG. 14 is a depiction of another embodiment of a pre-programming screen of the system of the present disclosure.

The other programming mode is for a medication therapy. At least two types of medication therapy groups exist: patient profiles, shown at step 122 of FIG. 15, and condition profiles, shown at step 120 in FIG. 15. Additionally, the programmer may enter drug parameters at step 124. FIG. 14 depicts a sample screen for the preprogramming of a patient profile for a specific preprogrammed medication therapy. In this screen, the programmer will enter at least one of a specific patient condition 138 and a disease state 140. For the specific profile parameters identified in the above programming step, the programmer will then enter program parameters for the medication therapy. As shown in FIG. 14, various program parameters are at least the drug 142, the volume for the therapy 144, the concentration 146 and the rate 150.

When the programmer completes the programming of either a drug therapy or a therapy profile, the programmer will be queried to either confirm the program or to re-program at step 116. If the programmer confirms, the system 110 proceeds to store the program to memory at step 118. Alternatively, if the programmer chooses to re-program, the system 110 reverts back to the start programming command at step 111.

It is also understood that the memory 14 of the present invention is capable of retrievably storing one or more medication therapies for at least one of a bolus dose medication therapy and a loading dose medication therapy. At least one of the stored medication therapies matches at least one set of patient profile parameters. The processor 16 provides for comparing the patient profile parameters to the medication therapies stored in the memory 14 at the processor 16. The processor 16 further provides for transmitting a medication therapy that matches the patient profile parameters.

Figure 16:
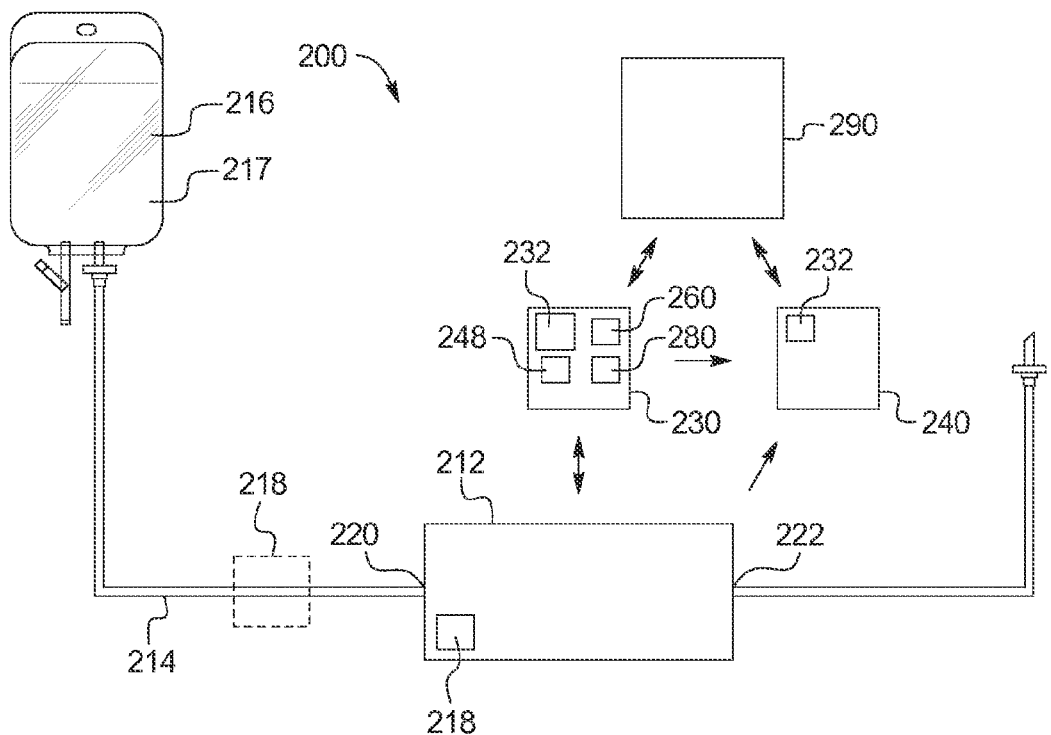
FIG. 16 is diagram of another embodiment of the present disclosure utilizing a disposable pump.
Figure 17:
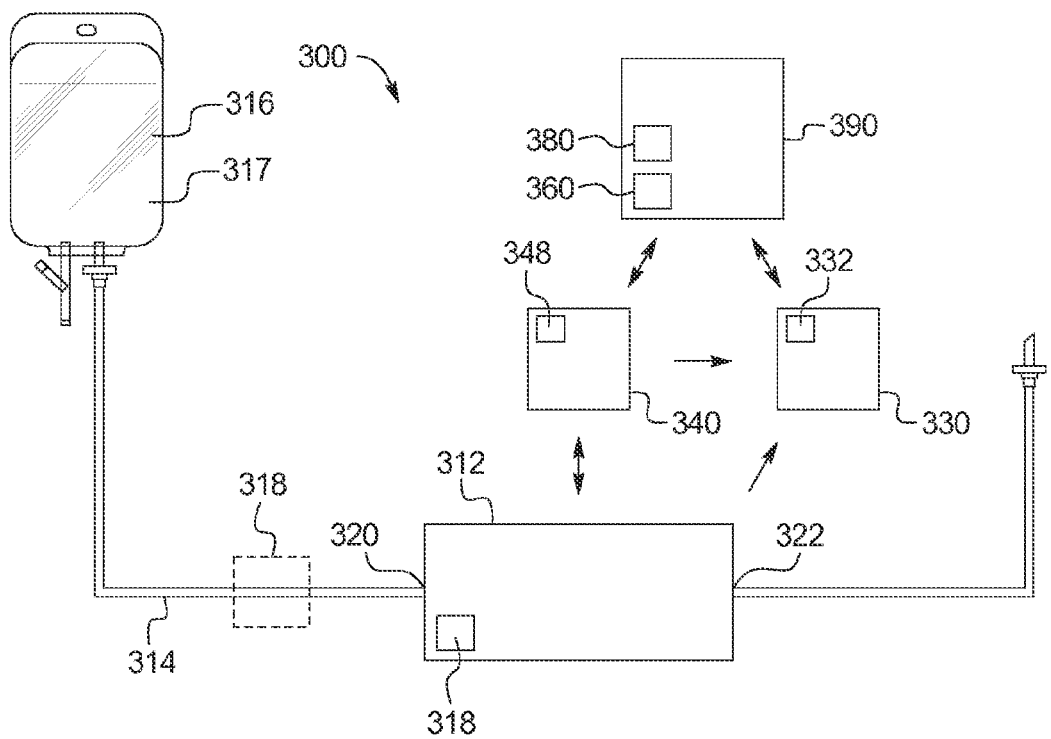
FIG. 17 is diagram of an even further embodiment of the present disclosure utilizing a disposable pump.

FIGS. 16 and 17 show additional embodiments of a system of the present invention, generally designated with the reference numerals 200 and 300. Similar to the embodiments described above in at least FIG. 3, the systems 200, 300 can utilize a disposable line set tubing 214, 314. As shown and described in greater detail in U.S. patent application Ser. No. 10/040,887, the entire specification of which is hereby incorporated by reference, the line set tubing 214, 314 can have attached to it a disposable element 212, 312, such as a disposable pump 212, 312. The line set tubing and/or the disposable pump can have an identifier 218, 318. In other words, the systems 200, 300 utilize a disposable element 212, 312 and an identifier 218, 318. The disposable pump can be a micro-pump or a MEMS (micro electromechanical system) pump, or other type of disposable pump. As shown in FIGS. 16 and 17, the systems 200, 300 generally include a medical pump 212, 312, preferably a MEMS pump, an administration line set 214, 314 and a container 216, 316.

MEMS stands for micro-electromechanical system (MEMS) component. MEMS is a technology used to create small or tiny devices which can be less than a millimeter in size, though they can also be larger as well. MEMS devices are typically fabricated from glass wafers or silicon, but the technology has grown far beyond its origins of the semiconductor industry. Each MEMS device is an integrated micro-system on a chip that can incorporate moving mechanical parts in addition to optical, fluidic, electrical, chemical and biomedical elements. Resulting MEMS devices or elements are responsive to many types of input, including pressure, vibration, chemical, light, and acceleration. The MEMS components can be a number of different elements including various types of pumps, a flow valve, a flow sensor, tubing, a pressure sensor or combinations of elements. These MEMS devices are smaller than conventional machines used for sensing, communication and actuation. As a result, it is possible to use them in places where mechanical devices could not traditionally be used. MEMS devices also work at a higher rate and consume less power than conventional devices. Additionally, MEMS technology has advanced to the stage that MEMS devices can be manufactured at a cost making it feasible to treat the devices as disposable or one-time use devices. MEMS devices are typically etched in silicon. It is further understood that MEMS may also describe other types of micro electromechanical system devices such as devices that are micro-molded in plastic. Thus, MEMS devices may include devices etched in silicon, molded in plastic or otherwise fabricated on a small scale. It should be understood that the MEMS element or pump can take a variety of different forms. For example, the MEMS element or pump can include be a disposable element such as a disposable peristaltic pump, volumetric pump, ambulatory pump, syringe pump or other type of disposable pump. The MEMS element can also be a micro-molded pump or element, or otherwise fabricated on a small scale. The MEMS element can also be a piezoelectrically actuated plastic element or pump. In certain embodiments, a flow sensor could be embedded into a pocket in the flow path of the disposable pump itself. It is also understood that the MEMS devices of the present invention application can be manufactured using Application Specific Integrated Circuit (ASIC) technology wherein electronics are etched on the same chip as the MEMS fluid structures.

The disposable element could be considered the MEMS pump 212 or the line set 214, or the combination of both elements. In addition, other types of MEMS components could also be used in the system 200. The container 216, 316 is a container similar to the container 84 described above in at least FIG. 3. In one preferred embodiment, the container 216, 316 is a flexible bag adapted to contain a medication, or medicament, such as a medical fluid. The administration line set 214, 314 is similar to the line set 25 described above. The line set 214, 314 includes a tubing having one end connected to or otherwise in communication with, the container 216, 316 and another end having a catheter or other device for communication with the patient.

As further shown in FIGS. 16 and 17, the MEMS pump 212, 312 is operably associated with the line set 214, 314. The MEMS pump 212, 312 may be connected to the line set 214, 314 in various configurations. For example, the MEMS pump 212, 312 may have an inlet port 220, 320 and an outlet port 222, 322 wherein the MEMS pump 212, 312 is connected at an intermediate portion of the line set 214, 314. Accordingly, a portion of the line set 214, 314 is connected to the inlet port 220, 320 and a portion of the line set 214, 314 is connected to the outlet port 222, 322 wherein the MEMS pump 212, 312 is operably connected to the line set 214, 314. Once properly connected, the MEMS pump 212, 312 can pump fluid from the container 216, 316, through the line set 214, 314 and to the patient.

The system 200, 300 may also use an identifier 218, 318. In one preferred embodiment, the identifier 218, 318 is associated with or otherwise connected to the MEMS pump 214, 314. It is understood, however, that the identifier 218, 318 may also be associated with other elements, and connected at other locations such as the disposable line set 214, 314 as shown in FIGS. 16 and 17. Various embodiments of the identifier 218, 318 are described in U.S. patent application Ser. No. 10/855,872, which is related to the present application and which has been incorporated by reference above, and can contain any of the information or identifying indicia or data as described therein. Additional embodiments of the identifier are described in U.S. patent application Ser. Nos. 10/748,589, 10/748,593, 10/748,749, 10/748,750, 10/748,762, 10/749,099, 10/749,101, and 10/749,102.

Referring to FIG. 16, the system 200 may further use a controller 230. The controller 230 can be operably associated with the MEMS pump 212 or other MEMS or disposable pump. The controller 230 may communicate with the MEMS pump 212 via a wireless connection. Alternatively, a hard connection may be utilized wherein the MEMS pump 212 may be plugged into the controller 230. It is further understood that the controller 230 can be integral as part of the MEMS pump 212. It is further understood that the controller 230 can be a separate hand-held computer or a separate network controller that controls the pump 212 via a network communication link, as will be explained below. As mentioned, the controller 230 has a recognition system 232. The recognition system 232 is capable of recognizing the data contained in the identifier 218. The recognition system 232 can cooperate with the identifier 218 to operate the system 200. For example, the identifier 218 may contain information that identifies the type of line set 214 connected to the MEMS pump 212.

In the embodiment shown in FIG. 16, similar to other embodiments described above, the controller 230 has a memory 260 and a microprocessor, microcontroller, or processor 280. A caregiving institution or hospital can preload the memory 260 with a plurality of patient profiles and condition profiles. The memory 260 can also have preloaded therein an associated medication therapy for each of the plurality of profiles. An input screen (not shown) on the controller can be used for receiving profile data, for example patient profile data and/or condition profile data, for a specific patient for which an infusion will be provided. The processor 280 compares the profile data received through the input screen to the preloaded profiles to determine if a correspondence exists between the two. For example, the algorithm used to determine if correspondence exists could include determining if an exact match exists, determining if the profile is within a group, determining if the profile is within a range, and/or determining if the profile is above or below a predetermined value. If correspondence exists, then the processor 280 provides at least one of the preloaded medication therapies from within the memory 260 for use within the operation of the pump 212 utilizing the corresponding preloaded therapy. Operation parameters associated with the corresponding therapy are used for implementing and controlling the infusion. The corresponding therapy and parameters can also be selected in a manner as described in prior embodiments.

As in prior embodiments, the controller 230 has a processor 280. As mentioned above, the controller 230 can communicate with the MEMS pump 212 and control the operation of the MEMS pump 212 via wireless communication or via wired communication. The controller 230 can also receive status information on the operation of the MEMS pump 212. As in the prior embodiments, the controller 212 also communicates with and controls the operation of a plurality of "channels" (not shown). For example, one controller 230 could communicate with and control the operation of a plurality of MEMS pumps 212 simultaneously, or in succession, depending on the therapy being provided to the patient.

The embodiment shown in FIG. 16 can further have a central computer 290, such as a server, and a portable user interface device or input device 240, such as a personal digital assistant (PDA). The user interface device 240 can bi-directionally communicate with the central computer 290. The central computer 290 and user interface device 240 can comprise various functions and structures which correspond to the various embodiments disclosed in U.S. patent application Ser. Nos. 10/748,589, 10/748,593, 10/748,749, 10/748,750, 10/748,762, 10/749,099, 10/749,101, and 10/749,102. In addition to the structure and functions explained herein, the controller 230 can additionally comprise the structure and functions of the various embodiments disclosed within these previously filed patent applications.

The user interface device or input device 240 can also be used for receiving the profile data, as can be performed through the input screen on the controller (should one be provided). For example, patient profile data and/or condition profile data, for a specific patient for which an infusion will be provided, can be entered through a screen on the user interface device 240. This profile data for a specific patient can be entered in a manner of the prior embodiments. This profile data for a specific patient can then be transmitted to the central computer 290, and further transmitted to the controller 230 for use in providing the infusion, as explained above. As a part of this process, the processor 280 would compare the profile data received through the user interface device 240 to the preloaded profiles within the memory 260 to determine if a correspondence exists.

As mentioned, the recognition system 232 of the controller 230 can recognize the identifier 218 of the line set 214 and/or MEMS pump 212. The user interface device 240 can also have a recognition system or reader 232, such as a bar code reader, for performing identical and/or related functions of the recognition system 232 of the controller 230. The controller 230 can also have a controller identifier 248 specific to that particular controller 230, such that the reader 232 of the user interface device 240 can be used to read each of the controller identifier 248, and the MEMS or line set identifier 218, and create an association between and among these devices and/or an operator (not shown, but typically the person logged into the user interface device 240), as shown and described in detail in the applications incorporated herein by reference above.

Status, alarm, alert, messages and/or other information relating to the operation of the MEMS pump 212 and/or the delivery of a medicament to a patient through the pump, received and/or generated by the controller 230 can be transmitted to the central computer 290 at a remote location through a communications network, such as a wireless communications network, as described in the applications mentioned above. This status and other information can be received by the interface device 240, and viewed and/or acted upon through the interface device 240 at a location near or remote from the controller 230, over a communications network, such as a wireless communications network, as explained in detail within the applications incorporated herein by reference. Likewise, the central computer 290 can be split into a first central computer and a second central computer according to functionality separation, data separation, or other separation, as explained in the incorporated applications.

A further embodiment of the present invention is shown in FIG. 17. In particular, instead of using a controller with a memory and processor therein, the system 300 comprises a MEMS communications interface device 340, and a memory 360 and processor 380 located in a separate device from the MEM interface device 340. In the embodiment shown, the memory 360 and processor 380 are located in a central computer 390 remote from but in communication with the MEMS interface device 340, over a communications network such as a wireless communications network. The MEMS interface device 340 can be operably associated with the MEMS pump 312 or other MEMS or disposable pump. The MEMS interface device 340 can communicate with the MEMS pump 312 via a wireless connection. Alternatively, a hard connection may be utilized wherein the MEMS pump 312 may be plugged into the MEMS interface device 340. It is further understood that the MEMS interface device 340 can be integral as part of the MEMS pump 312. It is further understood that the MEMS interface device 340 working in conjunction with the memory 360 and processor 380 can perform the same functions as the pump controller from the prior embodiments.

In the embodiment of FIG. 17, the MEMS interface device 340 has a recognition system 348. The recognition system 348 is capable of recognizing the data contained in the identifier 318. The recognition system 348 can cooperate with the identifier 318 to operate the system 300. For example, the identifier 318 may contain information that identifies the type of line set 314 connected to the MEMS pump 312.

In the embodiment shown in FIG. 17, similar to other embodiments described above, the system 300 has a memory 360 and a microprocessor, microcontroller, or processor 380. A caregiving institution or hospital can preload the memory 360 with a plurality of patient profiles and condition profiles. The memory 360 can also have preloaded therein an associated medication therapy for each of the plurality of profiles. An input screen (not shown) connected to the central computer 390 or to the MEMS interface device 340 can be used for receiving profile data, for example, patient profile data and/or condition profile data for a specific patient for which an infusion will be provided. The processor 380 compares the profile data received through the input screen to the preloaded profiles to determine if a correspondence exists between the two. For example, the algorithm used to determine if correspondence exists could include determining if an exact match exists, determining if the profile is within a group, determining if the profile is within a range, and/or determining if the profile is above or below a predetermined value. If correspondence exists, then the processor 380 provides at least one of the preloaded medication therapies from within the memory 360 for use within the operation of the pump 312 utilizing the corresponding preloaded therapy. Operation parameters associated with the corresponding therapy are used for implementing and controlling the infusion. The corresponding therapy and parameters can also be selected in a manner as described in prior embodiments.

As mentioned above, the MEMS interface device 340 can communicate with the MEMS pump 312 and control the operation of the MEMS pump 312, in conjunction with the memory 360 and the processor 380, via wireless communication or via wired communication. The interface device 340 can also receive status information on the operation of the MEMS pump 312. As in the prior embodiments, the interface device 340 also communicates with and controls the operation of a plurality of "channels" (not shown). For example, one interface device 340 could communicate with and control the operation of a plurality of MEMS pumps 312 simultaneously, or in succession, depending on the therapy being provided to the patient.

As mentioned, the embodiment shown in FIG. 17 has a central computer 390, such as a server, and a portable user interface device or input device 330, such as a personal digital assistant (PDA). The user interface device 330 can bi-directionally communicate with the central computer 390. The central computer 390 and user interface device 330 can comprise various functions and structures which correspond to the various embodiments disclosed in U.S. patent application Ser. Nos. 10/748,589, 10/748,593, 10/748,749, 10/748,750, 10/748,762, 10/749,099, 10/749,101, and 10/749,102. In addition to the structure and functions explained herein, the MEMS interface device 340, memory 360 and processor 380 can together comprise the structure and functions of the controller within the various embodiments disclosed above, and within these previously filed patent applications.

The user interface device or input device 330 can also be used for receiving the profile data, as can be performed through the input screen connected to the central computer 390 or MEMS interface device 340 (if provided). For example, patient profile data and/or condition profile data, for a specific patient for which an infusion will be provided, can be entered through a screen on the user interface device 330. This profile data for a specific patient can be entered in a manner of the prior embodiments. This profile data for a specific patient can then be transmitted to the central computer 390, and further transmitted to the MEMS interface device 340 for use in providing the infusion, as explained above. As a part of this process, the processor 380 would compare the profile data received through the user interface device 330 to the preloaded profiles within the memory 360 to determine if a correspondence exists.

As mentioned, the recognition system 348 of the MEMS interface device 340 can recognize the identifier 318 of the line set 314 and/or MEMS pump 312. The user interface device or input device 330 can also have a recognition system or reader 332, such as a bar code reader, for performing identical and/or related functions of the recognition system 348 of the MEMS interface device 340. The MEMS interface device 340 can also have a MEMS interface identifier 348 specific to that particular MEMS interface device 340, such that the reader 332 of the user interface device 330 can be used to read each of the MEMS interface identifier 348, and the MEMS or line set identifier 318, and create an association between and among these devices and/or an operator (not shown, but typically the person logged into the user interface device 330), as shown and described in detail in the applications incorporated herein by reference above. The system can be structured to utilize one and/or two dimensional bard codes, when bar codes are used.

Status, alarm, alert, messages and/or other information relating to the operation of the MEMS pump 312 and/or the delivery of a medicament to a patient through the pump, received and/or generated by the MEMS interface device 340 can be transmitted to the central computer 390 at a remote location through a communications network, such as a wireless communications network, as described in the applications mentioned above. This status and other information can be received by the user interface device 330, and viewed and/or acted upon through the user interface device 330 at a location near or remote from the MEMS interface device 340, over a communications network, such as a wireless communications network, as explained in detail within the applications incorporated herein by reference. Likewise, the central computer 390 can be split into a first central computer and a second central computer according to functionality separation, data separation, or other separation, as explained in the incorporated applications. As indicated above, it should be understood that the disposable element such as the MEMS pump 312 can be activated and controlled by the central computer 390.

The systems 200, 300 of FIGS. 16 and 17 further include a programming device to program the memory 260, 360 of the systems for preloading information on patient profiles and condition profiles, and associated medication therapies, and parameters therefore. In the system 200 of FIG. 16, this programming device can be a part of the controller 230, a part of the central computer 290, and/or a part of the user interface device 240. Once programmed by the programming device, the MEMS pump 212, 312 may be activated by the controller 230 or MEMS interface device 340. Once activated, the controller 230, or MEMS interface device 340, controls the MEMS pump 212, 312 wherein the pump 212, 312 operates to deliver medication to a patient. The pump 212, 312 has the ability to recognize a predetermined event such as when the fluid is generally substantially pumped from the container 216, 316 to define a generally empty container. For example, a predetermined pressure sensed by the MEMS pump 212, 312, once reached, could cause the MEMS pump 212, 312 to shut down. Once the MEMS pump 212, 312 shuts down, this condition could trigger alarms, alerts, or other messages to be sent to the central computer 290, 390, for further notification to the user interface device 240. In one embodiment, the memory 260, 360 and/or identifiers 218, 248, 318, 348 can comprise embedded or non-embedded electrically-alterable non-volatile memory, made by VIRAGE LOGIC under the name NOVEA and shown and described at http://www.viragelogic.com/products.

Additional features can be utilized with any of the embodiments described above. As discussed, a kit can be formed that may include the container 216, 316, the line set 214, 314 and the identifier 218, 318. The identifier 218, 318 can be associated with or connected to either of the container 216, 318 and the line set 214, 314. In some embodiments, the container 216, 316 may contain a pre-attached reconstitution device having a pre-attached drug container such as a vial. The reconstitution device could be activated to reconstitute the drug with the fluid 217, 317 in the container 216, 316. It is understood that the identifier 218, 318 can also include information regarding the vial that may be pre-attached to the reconstitution device. In another embodiment, a disposable pump such as a micro-pump or MEMS pump can also be connected to the line set 214, 314 and be considered as part of the kit. The identifier 218, 318 associated with such kits can have any of the information described above for overall proper operation of the system. In yet another embodiment, the container 216, 316, or container associated with the kit may include a pre-mixed medicament 217, 317.

In a further embodiment involving FIGS. 16 and/or 17, as indicated above, the identifier 218, 318 can be specifically programmed to include profile data for a specific patient, in addition to other information such as the patient identification for which the line set is intended, and/or the identification of the medicament 217, 317 within the container 216, 316. The reader 232 on the controller 230, the reader on the user interface device 240, 330, or a reader (not shown) on the MEMS interface device 340 can be used to automatically read the profile data and/or other information within the identifier 218, 318, and use this information to program and control the operation of the MEMS pump 212, 312 according to the preloaded medication therapy for the corresponding preloaded patient profiles and condition profiles. Through at least one of the controller 230, user interface 240, 330, and/or central computer 290, 390, the user can be given the opportunity to accept, reject, or modify the medication therapy suggested by the system 200, 300 as a result of the profile data being read from the identifier 218, 318.

It should understood that a pump utilized in the systems described above and below herein, can incorporate safety software. The safety software is capable of generating basic failure alarms wherein the pump would assume a fail safe condition such as no free flow of medicament through the pump. Various software/pump configurations may be utilized. For example, all software may be located on the pump head, or all software may be located off of, or remote from the pump head. In addition, all software may be located off of the pump head with the exception of the specific safety software being located on the pump head. In particular, and preferably, the controller 230 can include safety software for generating basic failure alarms, when the remaining functionality of the controller is not operating or is in a compromised state. In this case, the controller 230 would assume a fail safe condition preventing the free flow of medicament through the pump to which the controller 230 is controlling and providing for a basic level of alarms/alerts. Alternatively or additionally, the safety software can reside at the central computer 290, 390 to achieve this functionality as well, for example when control of the pump, such as a MEMS pump 212,312, is taking place directly from the central computer 290, 390. Alternatively or additionally, the safety software can reside at the pump or MEMS element 8612 to achieve this functionality as well, for example when at least some minimal level of control is provided at the pump or MEMS element 212, 312 level. These safety software embodiments can apply to least the embodiments shown in FIGS. 87 and 88 below in a similar fashion, located for example on the interface device 240, 330, the central computer 290, 390, and/or MEMS element 212, 312.

It should be emphasized that the above-described embodiments of the present invention, particularly, any "preferred" embodiments, are possible examples of implementations, merely set forth for a clear understanding of the principles of the invention. Many variations and modifications may be made to the above-described embodiment(s) of the invention without substantially departing from the spirit and principles of the invention. All such modifications are intended to be included herein within the scope of this disclosure and the present invention and protected by the following claims.

The invention is claimed as follows:

1. A controller for a programmable medical pump comprising:
   a memory including a plurality of preloaded infusion therapies, each preloaded infusion therapy including an infusion time program parameter and an infusion dose program parameter that specify how the medical pump is operated to provide a selected preloaded infusion therapy, the infusion time program parameter including a pre-established time limit and the infusion dose program parameter including a pre-established dosage limit;
   a device receiving
      a selection of one of the plurality of preloaded infusion therapies, and
      values for the program parameters of the selected preloaded infusion therapy including a numerical time value for the infusion time program parameter and a numerical dosage value for the infusion dose program parameter; and
   a processor configured to
      determine that the pre-established dosage limit for the infusion dose program parameter needs to be adjusted based on the numerical time value for the infusion time program parameter to form an adjusted dosage limit,
      replace the pre-established dosage limit for the infusion dose program parameter with the adjusted dosage limit,
      determine if the received numerical dosage value exceeds the adjusted dosage limit, and
      responsive to determining that the received numerical dosage value is within the adjusted dosage limit, cause the selected preloaded infusion therapy to be administered via the medical pump using the received values for the program parameters.

2. The controller of claim 1, wherein the processor is further configured to provide a notification if it is determined that the received numerical dosage value has exceeded the adjusted dosage limit.

3. The controller of claim 2, wherein the notification includes a soft alarm that enables the selected preloaded infusion therapy to be administered using the received numerical dosage value that exceeded the adjusted dosage limit.

4. The controller of claim 3, wherein the selected preloaded infusion therapy is administered using the received numerical dosage value that exceeded the adjusted dosage limit upon an authorization, and wherein the authorization can include at least one of a username and a password.

5. The controller of claim 2, wherein the notification includes a hard alarm that prevents the selected preloaded infusion therapy from being administered using the received numerical dosage value that exceeded the adjusted dosage limit.

6. The controller of claim 5, wherein the hard alarm is provided when the received numerical dosage value exceeds a first threshold, while a soft alarm is provided when the received numerical dosage value exceeds a second threshold, the second threshold being closer to the adjusted dosage limit than the first threshold.

7. The controller of claim 1, wherein each of the plurality of preloaded infusion therapies is at least one of a fluid bolus infusion therapy, a drug bolus infusion therapy, and a loading dose infusion therapy.

8. A method for operating a medical pump comprising:
receiving, at a processor, a selection of a preloaded infusion therapy from among a plurality of preloaded infusion therapies stored in a memory of the medical pump, each preloaded infusion therapy including an infusion time program parameter and an infusion dose program parameter that specify how the medical pump is operated to provide a selected preloaded infusion therapy, the infusion time program parameter including a pre-established time limit and the infusion dose program parameter including a pre-established dosage limit;
receiving, in the processor, profile data corresponding to a specific patient;
providing, via the processor, preset values for the program parameters based upon the selected preloaded infusion therapy and the profile data, the preset values including a numerical time value for the infusion time program parameter and a numerical dosage value for the infusion dose program parameter;
determining, via the processor, that the pre-established dosage limit for the infusion dose program parameter needs to be adjusted based on the numerical time value for the infusion time program parameter to form an adjusted dosage limit,
replacing, via the processor, the pre-established dosage limit with the adjusted dosage limit;
determining, via the processor, if the adjusted dosage limit is exceeded by the numerical dosage value; and
responsive to determining that the numerical dosage value is within the adjusted dosage limit, administering the selected preloaded infusion therapy via the medical pump using the numerical values for the infusion time program parameter and the infusion dose program parameter associated with the selected preloaded infusion therapy.

9. The method of claim 8, further comprising:
receiving an amended numerical dosage value;
determining if the amended numerical dosage value exceeds the adjusted dosage limit; and
responsive to determining that the amended numerical dosage value is within the adjusted dosage limit, administering the selected preloaded infusion therapy using the amended numerical dosage value.

10. The method of claim 8, wherein the received profile data includes patient profile data and condition profile data, and wherein the selected preloaded infusion therapy includes a preloaded patient profile and a preloaded condition profile.

11. The method of claim 10, wherein the selection of the preloaded infusion therapy includes:
selecting the preloaded patient profile associated with the selected preloaded infusion therapy from a plurality of possible preloaded patient profiles, the selected preloaded patient profile most closely matching the received patient profile data;
selecting the preloaded condition profile associated with the selected preloaded infusion therapy from a plurality of possible preloaded condition profiles, the selected preloaded condition profile most closely matching the received condition profile data; and
selecting the preloaded infusion therapy to be the one that includes the most closely matching preloaded patient profile and the most closely matching condition profile.

12. The method of claim 8, further comprising:
determining that the selected preloaded infusion therapy is to be administered on a first channel of the medical pump;
receiving a selection of a second preloaded infusion therapy from among the plurality of preloaded infusion therapies stored in the memory;
determining that the second selected preloaded infusion therapy is to be administered on a second channel of the medical pump;
receiving second profile data for the second selected preloaded infusion therapy corresponding to the specific patient;
determining a second pre-established time limit for the infusion time program parameter and a second pre-established dosage limit for the infusion dose program parameter based upon the second selected preloaded infusion therapy and the second profile data;
providing second preset values for the program parameters based upon the second selected preloaded infusion therapy and the second profile data, the second preset values including a second numerical time value for the infusion time program parameter and a second numerical dosage value for the infusion dose program parameter; and
administering the second selected preloaded infusion therapy via the second channel of the medical pump using the second preset values of the program parameters.

13. The method of claim 12, further comprising administering the selected second infusion therapy after the originally selected preloaded infusion therapy.

14. The method of claim 12, further comprising determining the second pre-established limits for the program parameters corresponding to the second selected preloaded infusion therapy based upon the originally selected preloaded infusion therapy.

15. A medical pump comprising:
a pump actuator;
a memory including a plurality of preloaded infusion therapies, each of the preloaded infusion therapies including a different configuration of an infusion time program parameter and an infusion dose program parameter based upon an associated infusion type, the program parameters configured to specify how the medical pump is operated to provide a selected preloaded infusion therapy, the infusion time program parameter including a pre-established time limit and the infusion dose program parameter including a pre-established dosage limit;

a device configured to receive
  patient profile data, condition profile data, and medication profile data corresponding to a specific patient, and
  values for the program parameters of a selected one of the preloaded infusion therapies including a numerical time value for the infusion time program parameter and a numerical dosage value for the infusion dose program parameter; and a processor configured to
  select one of the preloaded infusion therapies based upon the patient profile data, condition profile data, and the medication profile data,
  determine that the pre-established dosage limit for the infusion dose program parameter is to be adjusted based on the numerical time value for the infusion time program parameter to form an adjusted dosage limit,
  replace the pre-established dosage limit with the adjusted dosage limit;
  determine if the received numerical dosage value exceeds the adjusted dosage limit; and
  responsive to determining that the received numerical dosage value is within the adjusted dosage limit, operate the pump actuator using the received values for the program parameters of the selected one of the preloaded infusion therapies.

16. The medical pump of claim 15, further comprising:
a line set; and
an information identifier included with the line set, the information identifier identifying at least one of the patient profile data, condition profile data, the medication profile data, and the numerical time value and the numerical dosage value for the respective program parameters of the selected one of the preloaded infusion therapies.

17. The medical pump of claim 16, further comprising a reader configured to access the least one of the patient profile data, condition profile data, the medication profile data, and the numerical time value and the numerical dosage value of the respective program parameters of the selected one of the preloaded infusion therapies from the information identifier.

18. The medical pump of claim 17, wherein the processor is configured to control the pump actuator using the infusion time program parameter and the infusion dose program parameter of the selected one of the preloaded infusion therapies received from the reader.

19. The medical pump of claim 17, wherein the reader includes at least one of a bar code reader and a radio frequency identification ("RFID") reader.

20. The medical pump of claim 15, wherein
  the patient profile data includes at least one of a pain state, a chronologic age, an age group, and a gestational age for the specific patient,
  the condition profile data includes at least one of a medical condition and a medical disease state for the specific patient, and
  the medication profile includes at least one of a type of medication to be administered to the specific patient and a name of medication to be administered to the specific patient.

21. The controller of claim 1, wherein the processor is configured to use the pre-established dosage limit as a basis for determining the adjusted dosage limit.

* * * * *